(12) United States Patent
Vogelstein et al.

(10) Patent No.: US 6,677,312 B1
(45) Date of Patent: Jan. 13, 2004

(54) METHODS FOR RESTORING WILD-TYPE P53 GENE FUNCTION

(75) Inventors: Bert Vogelstein, Baltimore, MD (US); Suzanne Baker, Nutley, NJ (US); Eric R. Fearon, Guilford, CT (US); Janice M. Nigro, Nashville, TN (US)

(73) Assignee: The Johns Hopkins University, Baltimore, MD (US)

( * ) Notice: Subject to any disclaimer, the term of this patent is extended or adjusted under 35 U.S.C. 154(b) by 671 days.

(21) Appl. No.: 08/825,746

(22) Filed: Apr. 3, 1997

Related U.S. Application Data

(60) Division of application No. 08/035,366, filed on Mar. 22, 1993, which is a continuation-in-part of application No. 07/928,661, filed on Aug. 17, 1992, now abandoned, which is a continuation-in-part of application No. 07/860,758, filed on Mar. 31, 1992, now Pat. No. 5,362,623, which is a continuation-in-part of application No. 07/715,182, filed on Jun. 14, 1991, now abandoned, which is a continuation of application No. 07/446,584, filed on Dec. 6, 1989, now abandoned, which is a continuation-in-part of application No. 07/330,566, filed on Mar. 29, 1989, now abandoned.

(51) Int. Cl.[7] .................. A61K 48/00; C12N 15/00; C12N 15/63
(52) U.S. Cl. .................. 514/44; 536/23.5; 530/350; 435/320.1; 435/455
(58) Field of Search .................. 514/44; 536/23.5; 530/350; 435/320.1, 455

(56) References Cited

U.S. PATENT DOCUMENTS

| 5,087,617 A | 2/1992 | Smith | 514/44 |
| 5,248,671 A | 9/1993 | Smith | 514/44 |
| 5,532,220 A | 7/1996 | Lee et al. | 514/44 |

OTHER PUBLICATIONS

Anderson, W.F. Human Gene Therapy. Nature 392 (Supplement):25–30, Apr. 1998.*
Hodgson, C.P. Advances in Vector Systems for Gene Therapy. Exp. Opin. Ther. Patents 5(5):459–468, 1995.*
Miller, N. et al. Targeted Vectors for Gene Therapy. FASEB Journal 9:190–199, 1995.*
Verma, I.N. Gene Therapy—Promises, Problems and Prospects. Nature 389:239–242, Apr. 1998.*
Frommel, C. et al. An Estimate on the Effect of Point Mutation and Natural Selection on the Rate of Amino Acid Replacement in Proteins. Journal of Molecular Evolution 21:233–257, 1985.*
Ngo, J.T. et al. Computational Complexity, Protein Structure Prediction, and the Levinthal Paradox in The Protein Folding Problem and Tertiary Structure Prediction (Merz, ed.). Birkhauser, Boston, 1994.*
Bowie, J.U. et al. Deciphering the Message in Protein Sequences: Tolerance to Amino Acid Substitutions. Science 247: 1306–1310, Apr. 1998.*
Marshall, "Less Hype, More Biology Needed for Gene Therapy", Science, vol. 270, p. 1751, Dec. 1995.
Donahue et al., "Helper Virus Induced T Cell Lymphoma in Nonhuman Primates after Retroviral Mediated Gene Transfer" The Journal of Experimental Medicine, Vol 176, pp. 1125–1135, Oct. 1992.
Marshall, "Gene Therapy's Growing Pains", Science, vol. 269, pp. 1050–1055, Aug. 1995.
Andy Coghlan, "Gene dream fades away", Focus, New Scientist, pp. 14–15, Nov. 25, 1995.
Orkin & Motulsky "Report" Recommendations of the panel to assess the NIH investment in research on gene Therapy, Dec. 7, 1995.
Finlay et al. "The p53 Proro–oncogene canact as a suppressor of transopmation", Cell, vol. 57, pps. 1083–1093, Jun. 30, 1989.
Eliyahu et al., "Wild–type p53 can inhibit oncogene–mediated focus formation" Proc. Natl. Acad. Science USA., Vol 86, pps. 8763–8767, Nov. 1989.
Koshland, "p53 Sweeps Trhough Cancer Research", Science, 262:1958–1959 (1993).

* cited by examiner

*Primary Examiner*—Anne M. Wehb'
(74) *Attorney, Agent, or Firm*—Banner & Witcoff, Ltd.

(57) ABSTRACT

Methods are provided for restoring wild-type p53 gene function to a cell. Such methods include gene therapy. Typically, this will stop tumor cells from proliferating.

2 Claims, 11 Drawing Sheets

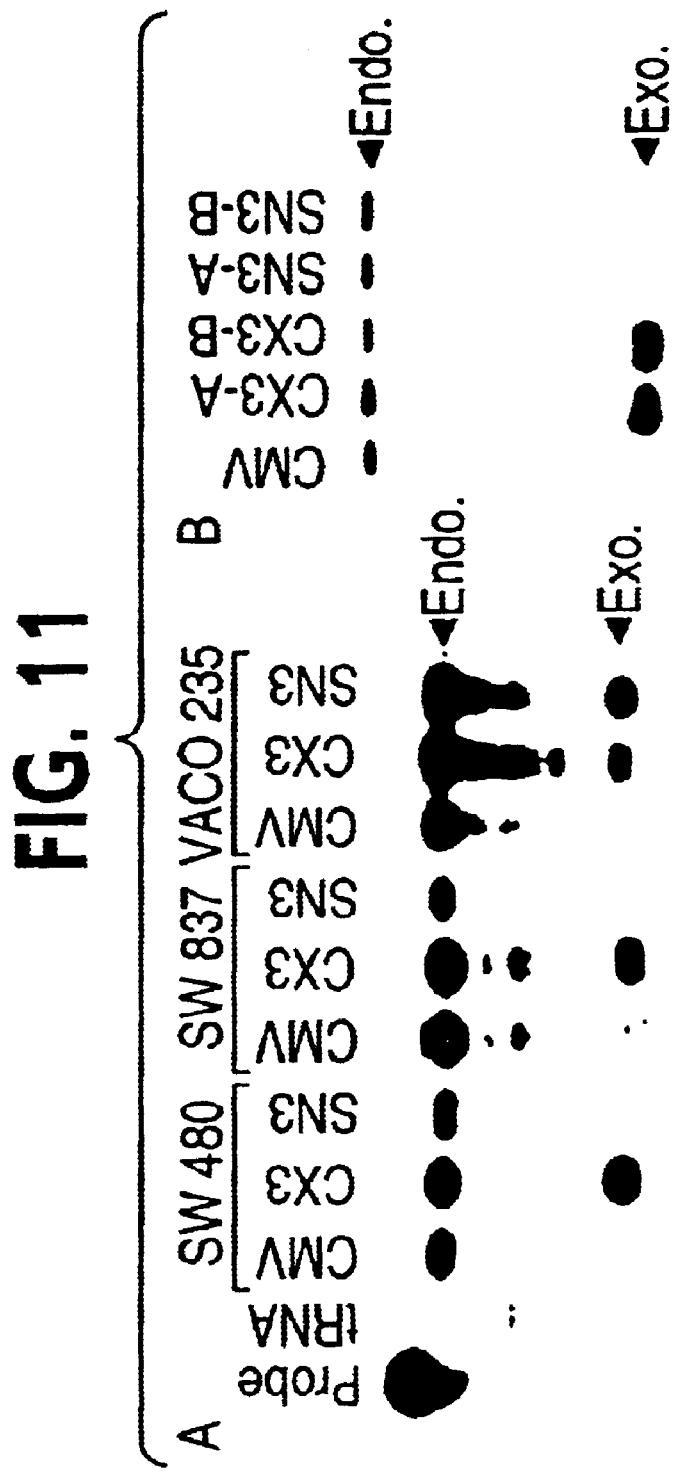

METHODS FOR RESTORING WILD-TYPE P53 GENE FUNCTION

This application is a divisional of Ser. No. 08/035,366, filed on Mar. 22, 1993, which is a continuation-in-part of Ser. No. 07/860,758, filed on Mar. 31, 1992, now U.S. Pat. No. 5,362,623, which is a continuation-in-part of Ser. No. 07/715,182, filed Jun. 14, 1991, now abandoned, as well as a continuation-in-part of Ser. No. 07/928,661, filed Aug. 17, 1992, now abandoned, which is a continuation of Ser. No. 07/446,584, filed Dec. 6, 1989, now abandoned, which is a continuation-in-part of Ser. No. 07/330,566, filed Mar. 29, 1989, now abandoned.

The U.S. Government has a paid-up license in this invention and the right in limited circumstances to require the patent owner to license others on reasonable terms as provided for by the terms of grant numbers GM07309, GM07184, HD20619, CA42857, CA28854, CA47527, CA35494, NS23427 and CA43460 awarded by the National Institutes of Health.

TECHNICAL AREA OF THE INVENTION

The invention relates to the area of cancer diagnostics and therapeutics. More particularly, the invention relates to detection and remediation of the loss and or alteration of wild-type p53 genes from tumor tissues.

BACKGROUND OF THE INVENTION

Recent studies have elucidated several genetic alterations that occur during the development of colorectal tumors, the most common of which are deletions of the short arm of chromosome 17 (17p). While some genetic alterations such as RAS gene mutations, appear to occur relatively early during colorectal tumor development, chromosome 17p deletions are often late events associated with the transition from the benign (adenomatous) to the malignant (carcinomatous) state. See Vogelstein et al., New England Journal of Medicine, Vol. 319, p525, 1988.

Because carcinomas are often lethal, while the precursor adenomas are uniformly curable, the delineation of the molecular events mediating this transition are of considerable importance. The occurrence of allelic deletions of chromosome 17p in a wide variety of cancers besides those of the colon, including those of the breast and lung, further emphasizes the importance of genes residing on chromosome 17p in the neoplastic process. Because allelic deletions have been reported to encompass a large area of chromosome 17p, there is a need in the art for defining the particular genetic region which is responsible for the neoplastic progression.

SUMMARY OF THE INVENTION

It is an object of the present invention to provide a method for diagnosing a neoplastic tissue of a human.

It is another object of the invention to provide a method of supplying wild-type p53 gene function to a cell which has lost said gene function.

It is yet another object of the invention to provide a kit for determination of the nucleotide sequence of the p53 gene by using the polymerase chain reaction.

It still another object of the invention to provide a nucleic acid probe for detection of mutations in the human p53 gene.

These and other objects of the invention are provided by one or more of the embodiments which are described below. In one embodiment of the present invention a method of diagnosing a neoplastic tissue of a human is provided comprising: isolating from a human a tissue suspected of being neoplastic; and detecting loss of wild-type p53 genes or their expression products from said tissue, said loss indicating neoplasia of the tissue.

In another embodiment of the present invention a method is provided for supplying wild-type p53 gene function to a cell which has lost said gene function by virtue of a mutation in the p53 gene, comprising: introducing a wild-type p53 gene into a cell which has lost said gene function such that said wild-type gene is expressed in the cell.

In yet another embodiment a kit is provided for determination of the nucleotide sequence of the p53 gene by polymerase chain reaction. The kit comprises: a set of pairs of single stranded DNA primers, said set allowing synthesis of all nucleotides of the p53 gene coding sequences.

In still another embodiment of the invention a nucleic acid probe is provided which is complementary to human wild-type p53 gene sequences and which can form mismatches with mutant p53 genes, thereby allowing their detection by enzymatic or chemical cleavage or by shifts in electrophoretic mobility.

The present invention provides the art with the information that the p53 gene is, in fact, the target of both deletional and point mutational alterations on chromosome 17p which are associated with the process of tumorigenesis. This information allows highly specific assays to be done to assess the neoplastic status of a particular tumor tissue as well as the performance of therapeutic anti-cancer methods.

BRIEF DESCRIPTION OF THE DRAWINGS

FIG. 11A shows expression analysis of pooled clones; the analysis was as described in FIG. 10.

FIG. 11B shows a Southern blot analysis of SW480 pooled clones.

DETAILED DESCRIPTION

Figure 1:
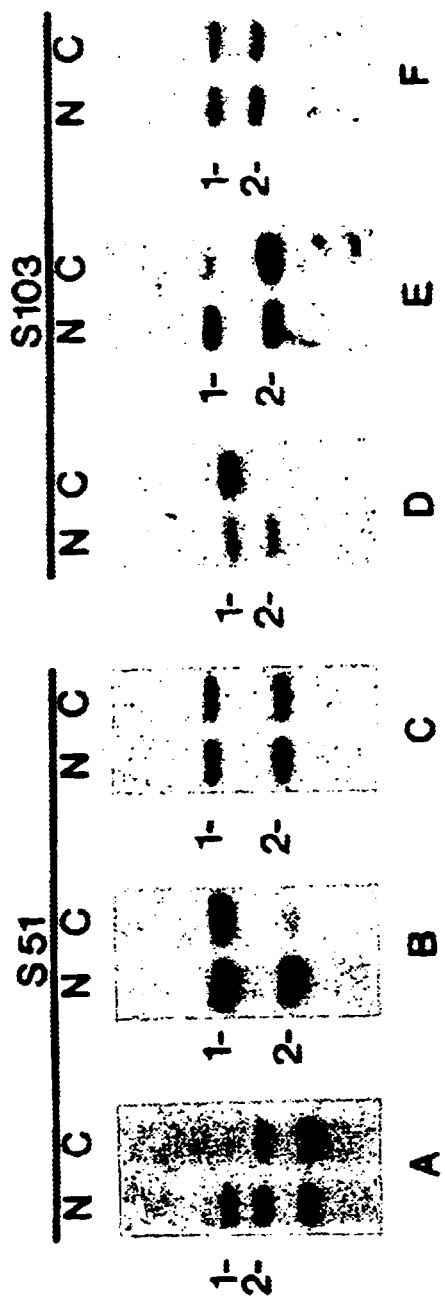
FIG. 1 demonstrates the analysis of allelic losses on chromosome 17p in the human tissue of two patients, S51 and S103.

It is a discovery of the present invention that mutational events associated with tumorigenesis occur in the p53 gene on chromosome 17p. Although it was previously known that deletion of alleles on chromosome 17p were common in certain types of cancers, it was not known that the deletions shared a common region which includes the p53 gene. Further it was not known that a second mutational event on the sister chromosome of that carrying the deletions was also affected by mutation in the p53 gene. The mutation of the sister chromosome does not involve gross rearrangements such as deletions, insertions or inversions, but rather point mutations located in a variety of positions throughout the p53 gene. Although the inventor does not wish to be bound by the following theory, it is proposed as a possible mechanism which explains the observed results. It is believed that the point mutation occurs first and the deletion event occurs second, as the latter event is correlated with the change of a tumor from an adenomatous to a carcinomatous state.

According to the diagnostic method of the present invention, loss of the wild-type p53 gene is detected. The loss may be due to either deletional and/or point mutational events. If only a single p53 allele is mutated, an early neoplastic state is indicated. However, if both alleles are mutated then a late neoplastic state is indicated. The p53 allele which is not deleted (i.e., that on the sister chromosome to the chromosome carrying the deletion) can be screened for point mutations, such as missense, and frameshift mutations. Both of these types of mutations would lead to non-functional p53 gene products. In addition, point mutational events may occur in regulatory regions, such as in the promoter of the p53 gene, leading to loss or diminution of expression of the p53 mRNA.

In order to detect the loss of the p53 wild-type gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the p53 allele (or alleles) present in the tumor tissue and sequencing that allele(s) using techniques well known in the art. Alternatively, the polymerase chain reaction can be used to amplify p53 gene sequences directly from a genomic DNA preparation from the tumor tissue. The DNA sequence of the amplified sequences can then be determined. The polymerase chain reaction itself is well known in the art. See e.g., Saiki et al., Science, Vol. 239, p. 487, 1988; U.S. Pat. No. 4,683,202; and U.S. Pat. No. 4,683,195. Specific primers which can be used in order to amplify the p53 gene will be discussed in more detail below.

Specific deletions of p53 genes can also be detected. For example, restriction fragment length polymorphism (RFLP) probes for the p53 gene or surrounding marker genes can be used to score loss of a p53 allele. Other techniques for detecting deletions, as are known in the art can be used.

Loss of wild-type p53 genes may also be detected on the basis of the loss of a wild-type expression product of the p53 gene. Such expression products include both the mRNA as well as the p53 protein product itself. Point mutations may be detected by sequencing the mRNA directly or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Alternatively, mismatch detection can be used to detect point mutations in the p53 gene or its mRNA product. While these techniques are less sensitive than sequencing, they are simpler to perform on a large number of tumors. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type p53 gene. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the p53 mRNA or DNA. The riboprobe need not be the full length of the p53 mRNA or gene but can be a segment of either. If the riboprobe comprises only a segment of the p53 mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, vol. 85, 4397, 1988; and Shenk et al., Proc. Natl. Acad. Sci. USA, vol. 72, p. 989, 1975. Alternatively, mismatches can be detected by shifts in the electrophoretic mobility of mismatched duplexes relative to matched duplexes. See, e.g., Cariello, Human Genetics, vol. 42, p. 726, 1988. With either riboprobes or DNA probes, the cellular mRNA or DNA which might contain a mutation can be amplified using PCR (see below) before hybridization.

DNA sequences of the p53 gene from the tumor tissue which have been amplified by use of polymerase chain reaction may also be screened using allele-specific probes. These probes are nucleic acid oligomers, each of which contains a region of the p53 gene sequence harboring a known mutation. For example, one oligomer may be about 30 nucleotides in length, corresponding to a portion of the p53 gene sequence. At the position coding for the 175th codon of p53 gene the oligomer encodes an alanine, rather than the wild-type codon valine. By use of a battery of such allele-specific probes, the PCR amplification products can be screened to identify the presence of a previously identified mutation in the p53 gene. Hybridization of allele-specific probes with amplified p53 sequences can be performed, for example, on a nylon filter. Hybridization to a particular probe indicates the presence of the same mutation in the tumor tissue as in the allele-specific probe.

Loss of wild-type p53 genes can also be detected by screening for loss of wild-type p53 protein function. Although all of the functions which the p53 protein undoubtedly possesses have yet to be elucidated, at least two specific functions are known. Protein p53 binds to the SV40 large T antigen as well as to the adenovirus E1B antigen. Loss of the ability of the p53 protein to bind to either or both of these antigens indicates a mutational alteration in the protein which reflects a mutational alteration of the gene itself. Alternatively, a panel of monoclonal antibodies could be used in which each of the epitopes involved in p53 functions are represented by a monoclonal antibody. Loss or perturbation of binding of a monoclonal antibody in the panel would indicate mutational alteration of the p53 protein and thus of the p53 gene itself. Any means for detecting an altered p53 protein can be used to detect loss of wild-type p53 genes.

Mutant p53 genes or gene products can also be detected in body samples, such as, serum, stool, or other body fluids, such as urine and sputum. The same techniques discussed above for detection of mutant p53 genes or gene products in tissues can be applied to other body samples. By screening such body samples, a simple early diagnosis can be achieved for many types of cancers. In addition, the progress of chemotherapy or radiotherapy can be monitored more easily by testing such body samples for mutant p53 genes or gene products.

The method of the present invention for diagnosis of neoplastic tissue is applicable across a broad range of tumors. These include lung, breast, brain, colorectal, bladder, mesenchyme, prostate, liver as well as stomach tumors. In addition the method may be used in leukemias and osteosarcomas. It thus appears that the p53 gene has a role in the development of a broad range of tumors. The methods of diagnosis of the present invention are applicable to any tumor in which p53 has a role in tumorigenesis. The diagnostic method of the present invention is useful for clinicians so that they can decide upon an appropriate course of treatment. For example, a tumor displaying loss of both p53 alleles suggests a more aggressive therapeutic regimen than a tumor displaying loss of only one p53 allele.

The kit of the present invention is useful for determination of the nucleotide sequence of the p53 gene using the polymerase chain reaction. The kit comprises a set of pairs of single stranded DNA primers which can be annealed to sequences within or surrounding the p53 gene in order to prime amplifying DNA synthesis of the p53 gene itself. The complete set allows synthesis of all of the nucleotides of the p53 gene coding sequences. The set of primers may or may not allow synthesis of both intron and exon sequences. However, it should allow synthesis of all exon sequences.

In order to facilitate subsequent cloning of amplified sequences, primers may have restriction enzyme sites appended to their 5' ends. Thus, all nucleotides of the primers are derived from p53 sequences or sequences adjacent to p53 except the few nucleotides necessary to form a restriction enzyme site. Such enzymes and sites are well known in the art. The primers themselves can be synthesized using techniques which are well known in the art. Generally, the primers can be made using synthesizing machines which are commercially available.

In a preferred embodiment, the set of primer pairs comprises five primer pairs which are listed below. Primer pair 1: 5'-GGAATTCCACGACGGTGACACG-3' (SEQ ID NO:1) and 5'-GGAATTCGGTGTGTAGGAGCTGCTGG-3' (SEQ ID NO:2); pair 2: 5'-GGAATTCCCAGAAT GCCAGAGGC-3' (SEQ ID NO:3); 5'-GGAATTCATGTGCTGTGACTGCTTG-3' (SEQ ID NO:4); pair 3: 5'-GGAATTCCACACCCCCGCCCG-3' (SEQ ID NO:5) and 5'-GGAATTCATGCCGCCCA TGCAG-3' (SEQ ID NO:6); pair 4: 5'-GGAATTCTGACTGTACCACCATCC-3' (SEQ ID NO:7)and 5'-GGAATTCTCCATCCAGTGGTTTC-3' (SEQ ID NO:8); pair 5: 5'-GGAATTCCCAACAAC CCAGCTCC-3' (SEQ ID NO:9) and 5'-GGAATTCAAAA TGGCAGGGGAGGG-3' (SEQ ID NO:10).

The nucleic acid probes provided by the present invention are useful in the RNase protection method for detecting point mutations already discussed above. They may also be used to detect mismatches with the p53 gene or mRNA using other techniques. Mismatches can be detected using other enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack, et al., Proc. Natl. Acad. Sci. USA, vol. 83, p. 586, 1986. If a riboprobe is used to detect mismatches with mRNA, it is complementary to the mRNA of the human wild-type p53 gene. The riboprobe thus is an anti-sense probe in that it does not code for the p53 protein because it is of the opposite polarity to the sense strand. The riboprobe generally will be radioactively labeled which can be accomplished by any means known in the art. If the riboprobe is used to detect mismatches with DNA it can be of either polarity, sense or anti-sense. Similarly, DNA probes also may be used to detect mismatches. Probes may also be complementary to mutant alleles of p53 gene. These are useful to detect similar mutations in other patients on the basis of hybridization rather than mismatches. These are discussed above and referred to as allele-specific probes.

According to the present invention a method is also provided of supplying wild-type p53 function to a cell which carries mutant p53 alleles. The wild-type p53 gene or a part of the gene may be introduced into the cell in a vector such that the gene remains extrachromosomal. In such a situation the gene will be expressed by the cell from the extrachromosomal location. If the mutant p53 genes present in the cell are expressed, then the wild-type p53 gene or gene portion should be expressed to a higher level than that of the mutant gene. This is because the mutant forms of the protein are thought to oligomerize with wild-type forms of the protein. (Eliyahu et al., Oncogene, Vol. 3, p. 313, 1988.) If a gene portion is introduced and expressed in a cell carrying a mutant p53 allele, the gene portion should encode a part of the p53 protein which is required for non-neoplastic growth of the cell. More preferred is the situation where the wild-type p53 gene or a part of it is introduced into the mutant cell in such a way that it recombines with the endogenous mutant p53 gene present in the cell. Such recombination would require a double recombination event which would result in the correction of the p53 gene mutation. Vectors for introduction of genes both for recombination and for extrachromosomal maintenance are known in the art and any suitable vector may be used.

According to another embodiment of the invention viral vectors can be used to introduce wild-type p53 alleles to cells. Such vectors are designed to express non-viral genes. Classes of such vectors include without limitation: retroviral vectors, adenoviral vectors, herpes virus vectors and adeno-associated virus vectors. These vectors can integrate into the genome and even after integration direct the expression of inserted genes, such as p53. Plasmid expression vectors can also be used. These may integrate into the genome or replicate autonomously, while directing the expression of p53.

Polypeptides or other molecules which have p53 activity may be supplied to cells which carry mutant p53 alleles. The active molecules can be introduced into the cells by microinjection or by liposomes, for example. Alternatively, some such active molecules may be taken up by the cells, actively or by diffusion. Supply of such active molecules will effect an earlier neoplastic state.

Predisposition to cancers can be ascertained by testing normal tissues of humans. For example, a person who has inherited a germline p53 mutation would be prone to develop cancers. This can be determined by testing DNA from any tissue of the person's body. Most simply, blood can be drawn and DNA extracted from the cells of the blood. Loss of a wild-type p53 allele, either by point mutation or by deletion, can be detected by any of the means discussed above. DNA can also be extracted and tested from fetal tissues for this purpose.

The following are provided for exemplification purposes only and are not intended to limit the scope of the invention which has been described in broad terms above.

EXAMPLES

Example 1

This example demonstrates that the deletions found on chromosome 17p in human colorectal carcinomas share a common region between bands 17p12 and 17p13.3.

Twenty DNA probes detecting restrictions fragment length polymorphisms (RFLPs) on chromosome 17p were used to examine the patterns of allelic losses in colorectal tumors. These probes have been mapped to seven discrete regions of 17p on the basis of their hybridization to human-rodent somatic cell hybrids containing parts of chromosome 17p (P. van Tuinen, D. C. Rich, K. M. Summers, D. H. Ledbetter, Genomics 1, 374 (1987); P. van Tuinen et al., Am. J. Hum. Gen. 43, 587 (1988); P. R. Fain et al., Genomics 1, 340 (1987); unpublished data of D. H. Ledbetter and D. F. Barker).

DNA was obtained from 58 carcinoma specimens and compared to DNA from adjacent normal colonic mucosa. Allelic losses were scored if either of the two alleles present in the normal cells was absent in the DNA from the tumor cells. Allelic deletions can be difficult to detect in DNA prepared from whole tumors because most solid tumors contain a significant number of non-neoplastic stromal and inflammatory cells. For this reason, regions of tumors containing a high proportion of neoplastic cells were identified histopathologically and isolated, and DNA was prepared from cryostat sections of these regions as described previously (S. Goelz, S. R. Hamilton, B. Vogelstein, Biochem. Biophys. Res. Commun. 130, 118 (1985); E. R. Fearon, A. Feinberg, S. R. Hamilton, B. Vogelstein, Nature 318, 377 (1985). Grossly normal colonic mucosa adjacent to the tumors was obtained from each patient and used to prepare control DNA.

The two parental alleles could be distinguished in the normal mucosa of each patient with at least 5 of the 20 RFLP markers (the "informative" markers for each case). Seventy-seven percent of the tumors exhibited allelic losses of at least 3 markers. Studies of 8 tumors which retained heterozygosity for some but not all markers on chromosome 17p enabled the definition of a common region of deletion.

FIG. 1 shows a sample of the data collected from two patients. DNA from normal (N) and carcinoma (C) tissue of patients S51 and S103 was digested with restriction endonucleases and the fragments separated by electrophoresis. After transfer to nylon filters, the DNA was hybridized to radiolabeled probes. Techniques used for DNA purification restriction endonuclease digestion, electrophoresis, transfer and hybridization were performed as described (B. Vogelstein et al., N. Engl. J. of Med. 319, 525 (1988); Goelz, supra; Fearon, supra.) TaqI digestion was used for panels A, B, C, and F, BamHI for panel D and MspI for panel E. Autoradiographs of the washed filters are shown. The alleles designated "1" and "2" refer to the larger and smaller polymorphic alleles, respectively, present in the normal DNA samples. The probes used were: A: MCT35.2; B: EW301; C: YNH137.3; D: YNZ22.1; E: MCT.35.1; F: EW505. Deletions of allele 1 can be seen in panels A and E; deletions of allele 2 in panels B and D.

Figure 2:
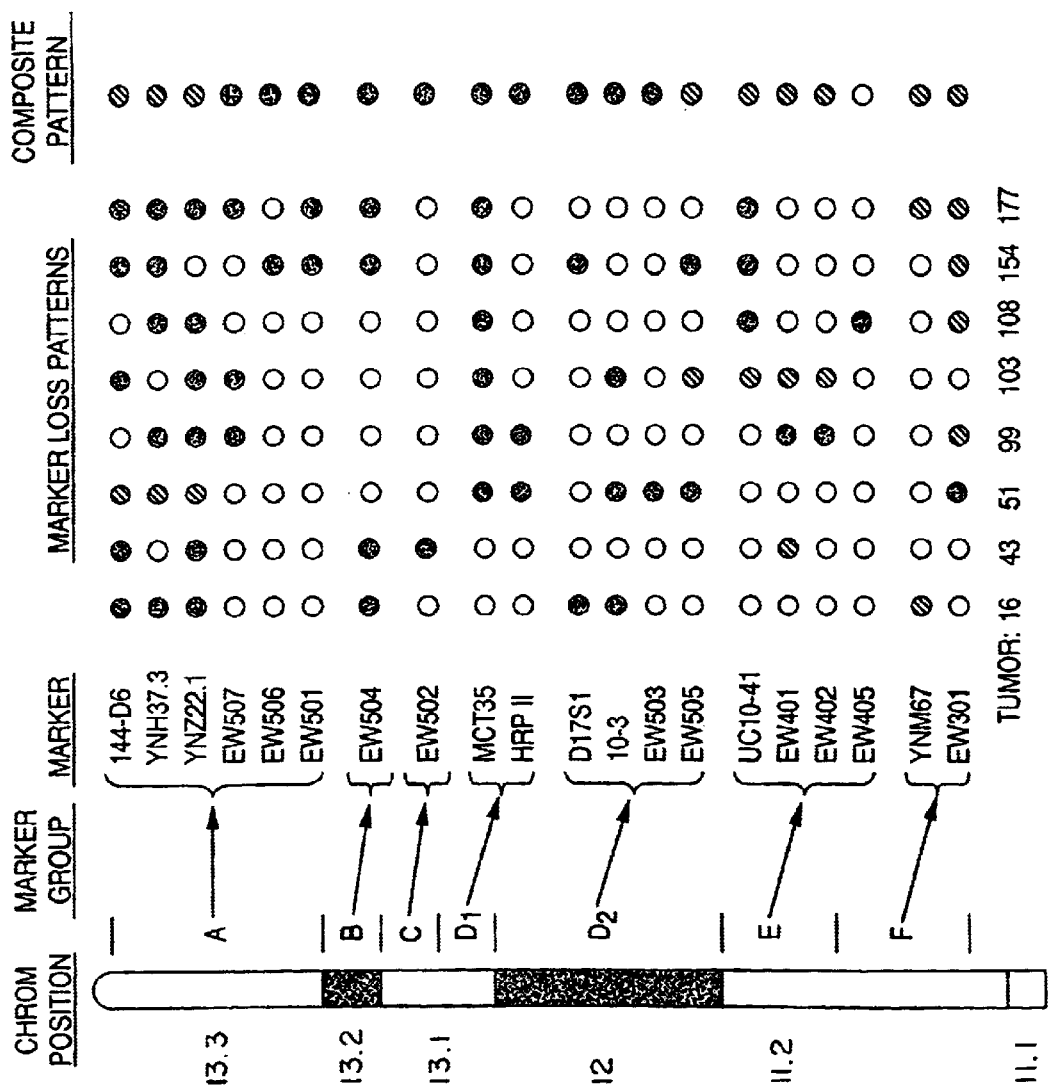
FIG. 2 shows a map of the common region of deletions on chromosome 17p in colorectal tumors. The chromosomal positions of 20 restriction fragment length polymorphism (RFLP) markers from chromosome 17p are indicated. The markers were previously mapped to seven sub-chromosomal regions (indicated A to F). Hybridization results for eight tumors are shown on the right, with patient identification numbers indicated at the bottom. A filled circle indicates loss of one parental allele in the tumor; a cross-hatched circle indicates retention of both parental alleles; an open circle indicates that the marker was not informative, i.e. the patient's normal tissue was not heterozygous for the marker. The premise of the composite pattern is that there is a single target gene on 17p. Therefore, markers for which heterozygosity was retained in any of the eight tumors (i.e., cross-hatched circles) would be outside the target locus.

The tumor from patient S51 had retained both parental alleles of three markers from the distal region of 17p, but had lost one of all more proximal markers that were formative (FIGS. 1, A–C). This implied that the target of the allelic loss in this tumor was proximal to the three retained markers. Analysis of the pattern of marker loss is shown in FIG. 2. The tumor from patient S103 had retained both parental alleles at all informative loci proximal to EW505, but had allelic deletions of several more distal markers (FIGS. 1, D–F). The combined data depicted in FIG. 2 indicated that the smallest common region of deletion extended between markers within band 17p12 to those within band 17p13.3. This localization is based on the assumption that the same 17p locus was the target of deletion in all of the tumors.

Example 2

This example demonstrates that the non-deleted p53 alleles in colorectal carcinomas carrying a p53 deletion are not rearranged.

First, p53 cDNA probes detecting exons spread over 20,000 base pairs (including all protein encoding exons) [P. Lamb, L. V. Crawford, Mol. Cell. Biol. 6, 1379 (1986); R. Zakut-Houri, B. Bienz-Tadmor, D. Givol, M. Oren, EMBO J. 4, 1251 (1985); N. Harris E. Brill, O. Shahat, M. Prokocimer, T. E. Admas, Mol. Cell. Biol., 6, 4650 (1986); G. Matlashewski et al., Molec. Cell. Biol. 7, 961 (1987); V. L. Buchman et al., Gene 70, 245 (1988)] were used to examine the DNA of 82 colorectal carcinomas (50 primary specimens and 32 cell lines) in Southern blotting experiments.

No rearrangements of the p53 gene were observed with EcoRI or BamHI digests, nor were deletions of both alleles seen. Because p53 expression might be affected by gross genetic alterations further removed from p53 coding sequences, pulsed-field gel electrophoresis was used to examine large restriction fragments encompassing the p53 gene. The restriction endonucleases EcoRV, PaeR7 I, NotI, and SalI generated p53 gene-containing fragments of 45–350 kb from the DNA of normal cells. No alterations were detected in the DNA from any of 21 colorectal tumor cell lines examined with each of these four enzymes.

Example 3

This example demonstrates that the non-deleted p53 alleles in colorectal carcinomas carrying a p53 deletion express mRNA of the normal size and in most cases normal amounts.

Northern blot experiments were performed on RNA from 22 colorectal tumors (6 primary tumors and 16 cell lines). Because p53 expression has been correlated with cellular growth and/or transformation other genes whose expression is similarly regulated were used as controls (c-myc, histone H3, and phosphoglycerate kinase).

RNA was purified from grossly normal colonic mucosa, primary carcinoma specimens or tumor cell lines, and separated by electrophoresis. Cell lines were generously provided by D. and M. Brattain or obtained from the American Type Culture Collection, Rockville, Maryland. Total cellular RNA was isolated by the acid-guanidinium extraction method (P. Chomczynski, N. Sacchi, Anal. Biochem. 162, 156 (1987)). Five micrograms were separated by electrophoresis through a 1.5% 2(N-morpholino) ethane sulfonic acid-formaldehyde agarose gel and electrophoretically transferred to nylon filters. The RNA was transferred to nylon filters and hybridized with a radiolabeled p53 gene probe. Labelling of the probes, hybridization, washing and autoradiography were performed as described. (Fearon et al., Science, Vol. 238, p. 193, 1987; Vogelstein et al., N. Engl. J. of Med., Vol. 319, p. 525, 1988; and Goelz, supra; and Fearon, Nature, supra . Autoradiographs were exposed for 18–24 hours.

Figure 3:
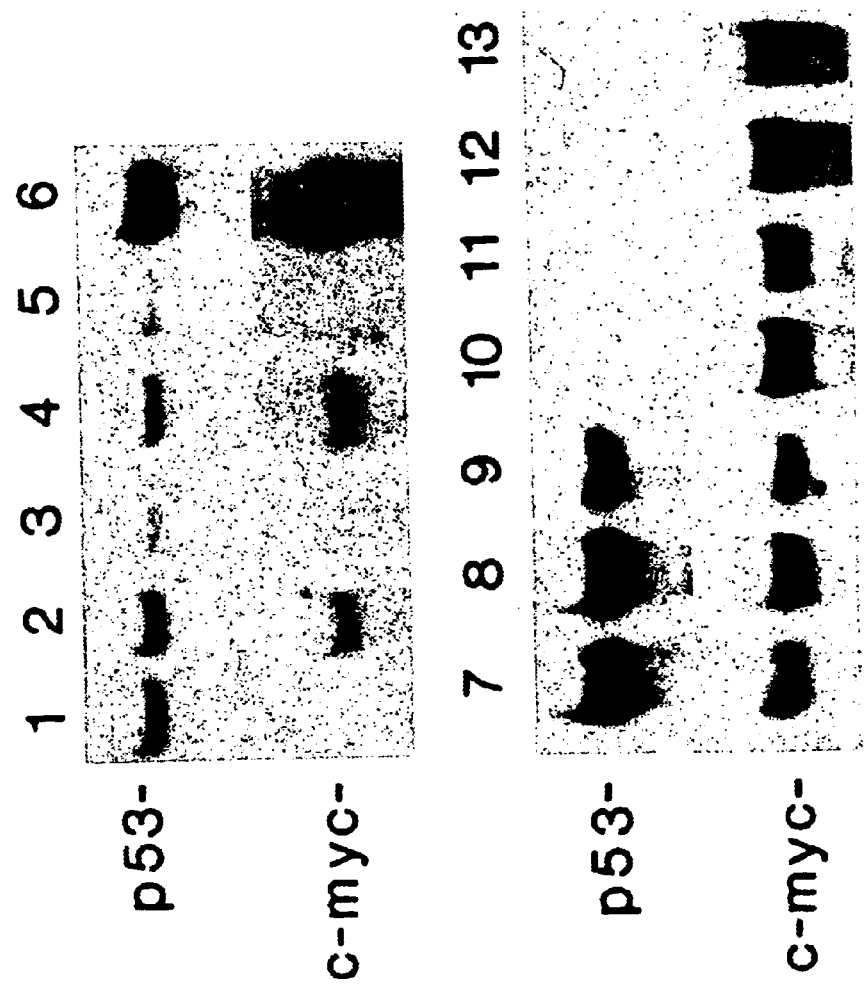
FIG. 3 shows a Northern blot analysis of p53 mRNA in colorectal tumors. The RNA in lanes 1–6 and 12 was prepared from human tissues (normal colonic mucosa (N) or carcinoma biopsies (C)). The RNA in lanes 7–11 and 13 was prepared from colorectal carcinoma cell lines.

The p53 probe was a 1.8 kb Xbal fragment of a p53 cDNA clone generously provided by D. Givol (EMBO J., vol. 4, p. 1251 (1985)). The c-myc probe was a 1.6 kb genomic Sstl fragment containing exon 2 of c-myc (K. Alitalo et al., Proc. Nat'l. Acad. Sci. USA 80, 1707 (1983)). The signals were removed from the filter, and the blot was re-hybridized with a c-myc gene probe. Autoradiographs of the hybridized filters are shown in FIG. 3. The size of the p53 mRNA detected was 2.8 kb, and the size of the c-myc mRNA was 2.5 kb.

The RNA in lanes 1–6 and lane 12 was prepared from human tissues (normal colonic mucosa (N) or carcinoma biopsies (C)). The RNA in lanes 7–11 and 13 was prepared from colorectal carcinoma cell lines. Lanes 1, 2: Patient S345, N and C, respectively. Lanes 3, 4: Patient S353, N and C, respectively. Lanes 5, 6, Patient S369, N and C, respectively. Lane 7: SW837, Lane 8: SW480, Lane 9: LoVo, Lane 10: SW948, Lane 11: SW1417, Lane 12: Patient S115, C, Lane 13: RKO.

The size of p53 mRNA was normal (2.8 kb) in all 22 tumors. Moreover, the relative abundance of p53 gene mRNA was usually at least as great in colorectal tumor cells as in normal colonic mucosa confirming the results of Calabretta et al. (Cancer Research, Vol. 46, p. 738 (1986)). However, in four tumors, (lanes 10–13) relatively little expression of p53 mRNA was observed compared to that in the other tumors. This low level of expression of p53 was specific in that c-myc, histone H3, and phosphoglycerate kinase mRNAs were expressed in these four tumors at levels similar to those seen in other colorectal tumors and at least as high as in non-neoplastic colonic mucosa.

Example 4

This example demonstrates that the non-deleted p53 allele in a primary tumor carries a point mutation at codon 143.

A tumor was chosen which had an allelic deletion of chromosome 17p yet expressed significant quantities of p53 mRNA. A cDNA clone originating from the remaining p53 allele was isolated and sequenced to determine whether the gene product was abnormal.

For practical reasons, a nude mouse xenograft (Cx3) of a primary tumor was selected for this test. Primary tumors contain non-neoplastic cells which could contribute p53 mRNA, while in xenografts the non-neoplastic cells (derived from the mouse) could not be the source of a human p53 cDNA clone. Cx3, like over 75% of colorectal carcinomas, had allelic deletions of several RFLP (restriction fragment length polymorphism) markers on chromosome 17 and expressed significant amounts of p53 mRNA.

A nearly full-length p53 cDNA was cloned from Cx3 mRNA using standard techniques. Double stranded cDNA was synthesized as described by U. Gubler and B. J. Hoffman, Gene 25 263 (1983) and cloned into the lambda gt10 vector. The cDNA insert was subcloned into Bluescript KS (Stratagene Cloning Systems, LaJolla, Calif.) and nested deletions were made with exonuclease III (S. Henekoff, Gene 28, 351 [1984]). Sequences were obtained from double-stranded templates using modified T7 polymerase as described by S. Tabor and C. C. Richardson, Proc. Nat'l. Acad. Sci. USA 84, 4767 (1987) and R. Kraft, J. Tardiff, K. S. Krauter and I. A. Leinwand, Biotechniques 6, 544 (1988).

The clone extended 2567 nucleotides from position −198 relative to the translation initiation site to the polyadenosine tail. The clone was sequenced by the dideoxy chain-termination method and one nucleotide difference was identified in comparison with published p53 cDNA sequences (See, Lamb, supra; Zakut-Houri, supra; Harris, supra; Matlashewski; supra; and Buchman, supra . A transition from T to C had occurred within codon 143 (GTG to GCG), resulting in a change of the encoded amino acid from valine to alanine.

To ensure that the sequence change was not an artifact of cDNA cloning, the polymerase chain reaction [PCR, (Saiki, et al., Science, Vol. 239, p. 487, 1988)] was used to amplify a 111 base pair (bp) sequence surrounding the presumptive mutation from genomic DNA of Cx3.

DNA was incubated in the presence of Taq polymerase with primer oligomers complementary to sequences 68 base pairs upstream and 43 base pairs downstream of codon 143. The upstream primer used was 5'-TTCCTCTTCCTGCAGTACTCC-3' (SEQ ID NO:11); all but 6 nucleotides of this primer were derived from the p53 intron 4 sequence determined by Buchman et al., supra. The downstream primer was 5'-GACGCGGGTGCCGGGCGG-3' (SEQ ID NO:12). After 35 cycles of denaturation (one minute, 93°), annealing (2 minutes, 55°) and elongation (2 minutes, 70°) amplified DNA fragments of 111 bp were generated. Following electrophoresis, the 111 bp amplified fragments were eluted from a polyacrylamide gel and purified by extraction with phenol and chloroform.

Analysis of the PCR product was facilitated by the observation that the presumptive mutation created a new HhaI site (GCGC at nt 427–430). An aliquot of each of the purified DNA fragments was digested with HhaI, separated by electrophoresis on a non-denaturing polyacrylamide gel, and electrophoretically transferred to nylon filters. The fragments were hybridized with a radioactive p53 probe generated from a 1.8 kb XbaI fragment of a p53 cDNA clone provided by D. Givol (Zakot-Houri, supra .

Figure 4:
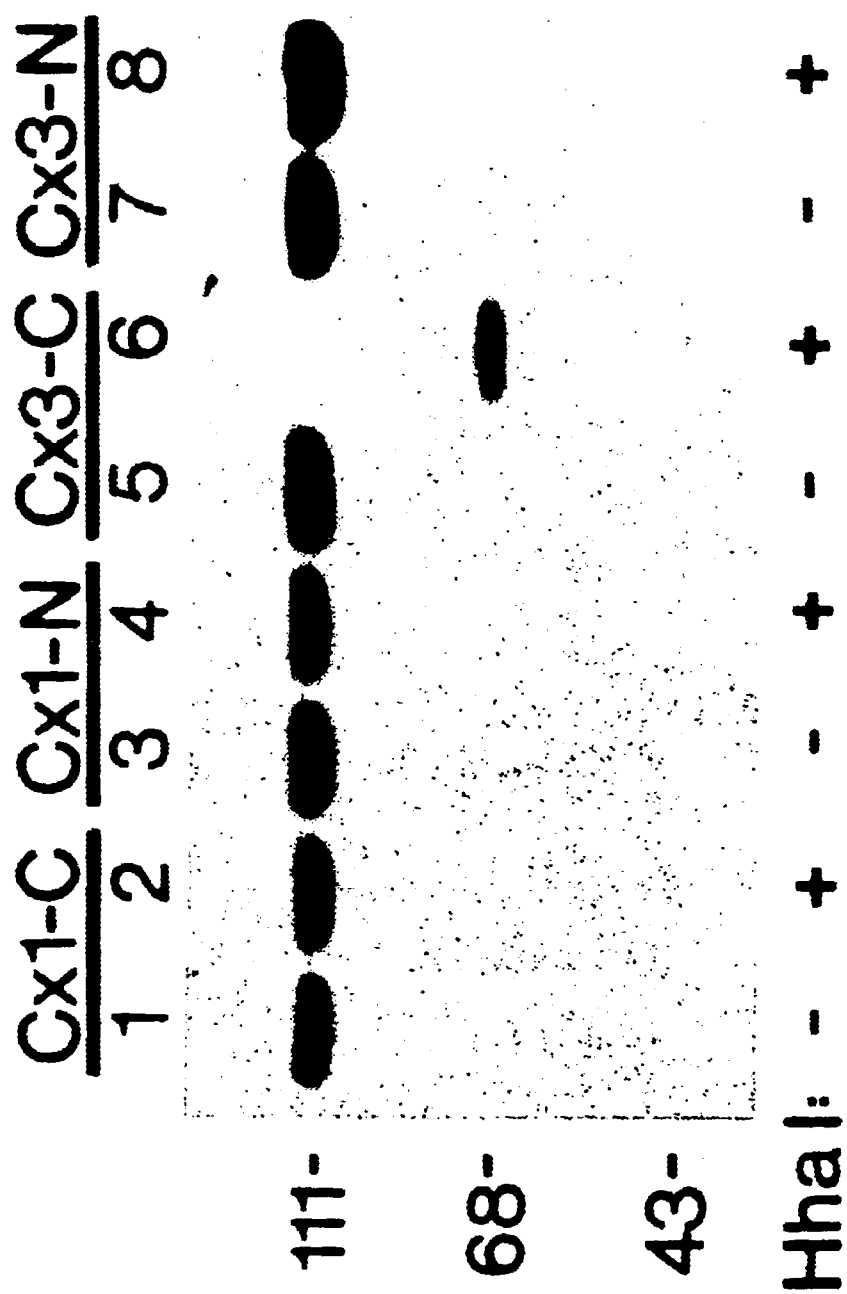
FIG. 4 shows analysis of the products of polymerase chain amplification of a 111 bp fragment surrounding the p53 gene codon 143. Lanes 1,2: colorectal tumor xenograft Cx1; lanes 3,4: normal fibroblasts from the patient providing Cx1; lanes 5,6: colorectal tumor xenograft Cx3; lanes 7,8: normal fibroblasts from the patient providing Cx3.

The 111 bp PCR product from tumor Cx3 was cleaved with HhaI to produce the expected 68 and 43 subfragments (FIG. 4, lanes 5 and 6). The 111 bp PCR product from the DNA of normal cells of the patient providing Cx3 was not cleaved with HhaI (lanes 7 and 8), nor were the PCR products of 37 other DNA samples prepared from the normal tissues, primary colorectal tumors, or xenografts of other patients (examples in FIG. 4, lanes 1–4). Therefore, the valine to alanine substitution present in this tumor was the result of a specific point mutation not present in the germline of the patient.

A small amount of a contaminating 73 base pair PCR product was present in most of the eluates; the contaminant was not cleaved by HhaI, however, so that it did not interfere with the analysis.

Example 5

Colorectal carcinoma xenograft Cx1, like Cx3, had allelic deletions of several markers on chromosome 17p and expressed considerable amounts of normal size p53 mRNA. First strand cDNA was generated from Cx1 RNA using random hexamers in the presence of reverse transcriptase (E. Noonan and I. B. Roninson, Nucleic Acids Research 16, 10366 [1988]). This cDNA was used in five separate PCR reactions to generate fragments corresponding to nucleotides −59 to 246 (primer pair 1), 189 to 508 (primer pair 2), 443 to 740 (primer pair 3), 679 to 979 (primer pair 4), and 925 to 1248 (primer pair 5). These fragments contained all coding sequences of the p53 gene. Primer pair 1: 5'-GGAATTCCACGACGGTGACACG-3' (SEQ ID NO: 1) and 5'-GGAATTCGGTGTAGGAGCTGCTGG-3' (SEQ ID NO:2); pair 2: 5'-GGAATTCCCAGAATGCCAGAGGC-3' (SEQ ID NO:3) and 5'-GGAATTCATGTGCTGTGACTGCTTG-3' (SEQ ID NO:4); pair 3: 5'-GGAATTCCACACCCCCGCCCG-3' (SEQ ID NO:5) and 5'-GGAATTCATGCCGCCCATGCAG-3' (SEQ ID NO:6); pair 4: 5'-GGAATTCTGACTGTACCACCATCC-3' (SEQ ID NO:7) and 5'-GGAATTCTCCATCCAGTGGTTTC-3' (SEQ ID NO:8); pair 5: 5'-GGAATTCCCAACAACACCAGCTCC-3' (SEQ ID NO:9) and 5'-GGAATTCAAAATGGCAGGGGAGGG-3' (SEQ ID NO:10). All primers had extraneous nucleotides comprising EcoRI cleavage sites at their 5' ends to facilitate cloning. The PCR products were cloned in the EcoRI site of Bluescript SK and sequenced as described in Example 4. Only 1 base pair change was identified (transition from CGC to CAC) and this change at codon 175 was found in two independent clones.

Figure 5:
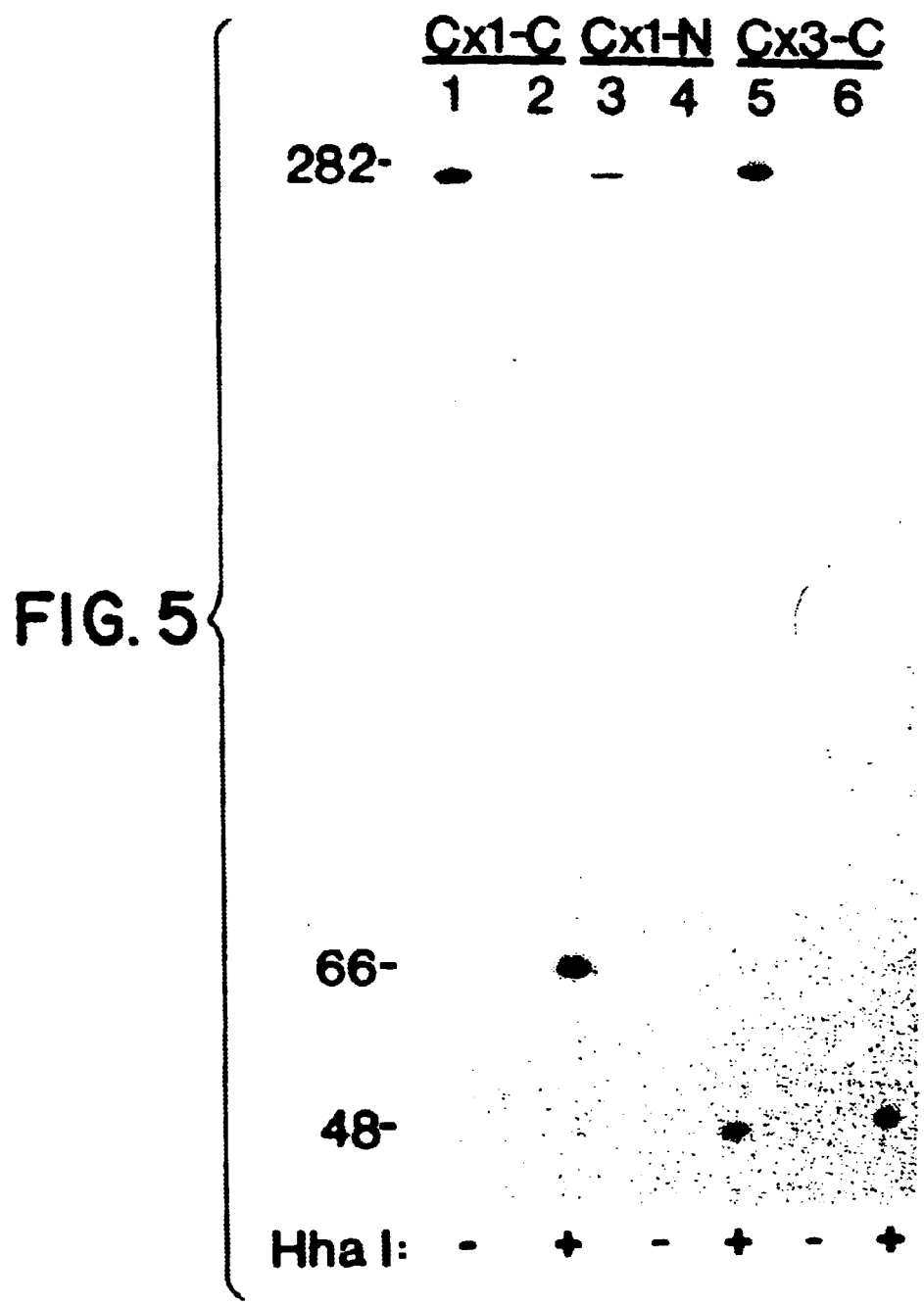
FIG. 5 shows polymerase chain reaction analysis of p53 codon 175. Lanes 1,2: colorectal tumor xenograft Cx1; lanes 3,4: normal fibroblasts from the patient providing Cx1; lanes 5,6: colorectal tumor xenograft Cx3. Samples in even numbered lanes only were digested with Hha I.

To ensure that the sequence change represented a mutation rather than a sequence polymorphism, PCR was used to amplify a fragment containing codon 175 from the genomic DNA of tumor Cx1 and normal cells. PCR was used to amplify a 319 bp fragment containing intron 5 and surrounding exon sequences. The upstream primer was the same as used for primer pair 3 and the downstream primer was 5'-CGGAATTCAGGCGGCTCATAGGGC-3' (SEQ ID NO: 13); PCR was performed as described in Example 4. Following electrophoresis through a 2% agarose gel, the 319 bp fragment was purified by binding to glass beads (Vogelstein et al., Proc. Nat'l. Acad. Sci. USA, Vol. 76, p. 615 (1979)). The DNA fragments were cleaved with StyI at nt 477 and end-labeled by fill-in with the Klenow fragment of DNA Polymerase I and $^{32}$P-dCTP. Following electrophoresis of the reaction mixture through a non-denaturing polyacrylamide gel, the 282 bp StyI fragment (nt 477–758), labeled at the proximal end and containing codon 175, was eluted and purified by extraction with phenol and chloroform. A portion of the eluted DNA was cleaved with HhaI and the fragments separated by electrophoresis on a 6% sequencing gel. The presumptive mutation abolished the HhaI site normally present at codon 175 (GCGC at nt 522 to 525). Thus, HhaI cleavage of the PCR products from DNA of the normal cells of the patient providing Cx1 (FIG. 5, lanes 3 and 4) or from the tumor of another patient (lanes 5 and 6) produced only the 48 bp product expected if codon 175 was wild-type. In contrast, the PCR product from tumor Cx1 was not cleaved at nt 524 (corresponding to codon 175) and exhibited only a larger 66 bp fragment resulting from cleavage at a normal downstream HhaI site at nt 542. Analysis of the PCR product from paraffin embedded samples of the primary tumor and liver metastasis also exhibited the diagnostic 66 bp HhaI fragment indicating the presence of a mutation.

Example 6

This example shows that five out of twenty-one carcinomas tested with the RNase protection method produced mRNA molecules with detectable sequence mismatches to the wild-type p53 RNA sequence.

Hybrids between a p53 anti-sense RNA probe and p53 mRNA should be cleaved by RNase A only at sequence mismatches. Although this method is not as definitive or as sensitive as sequencing, it allows rapid screening of a larger number of tumors. Twenty-one colorectal carcinomas (6 primary tumors and 15 cell lines) were examined with probes that included most of the p53 coding region.

Ten ug of cellular RNA was hybridized with radiolabeled anti-sense p53 RNA probe, and the hybrids digested with RNase A. A $^{32}$P-labelled RNA probe was generated in vitro from a p53 cDNA subclone in Bluescript (Stratagene Cloning Systems, La Jolla, Calif.). The probe included 561 nt of p53 mRNA coding sequence (nt 473–1034 relative to the translation start site) plus 60 nt derived from the vector.

Figure 6:
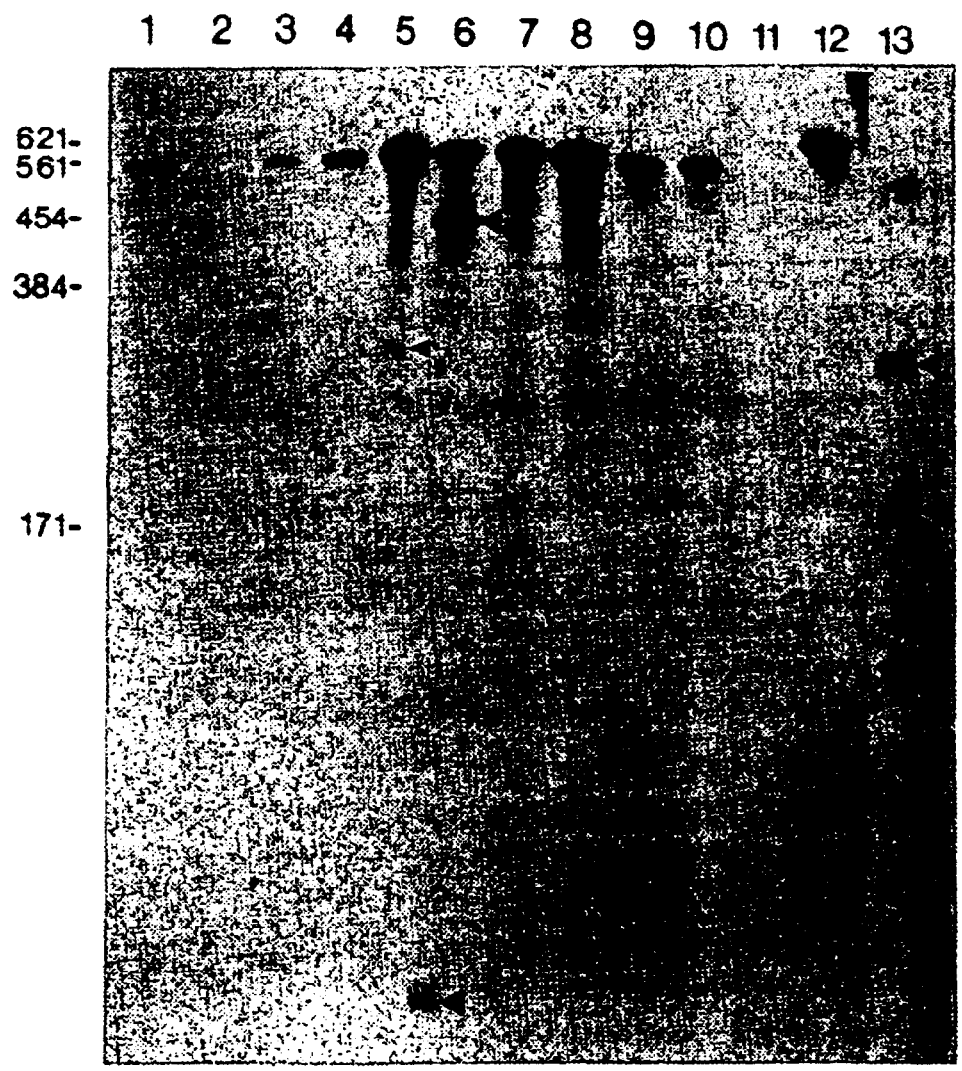
FIG. 6 depicts RNase protection analysis of p53 mRNA. Cellular RNA was hybridized with radiolabeled anti-sense p53 RNA probe, and the hybrids digested with RNase A. The RNA was derived from: lane 1: S115, carcinoma biopsy; lane 2: SW1417; lane 3: SW948; lane 4: RKO; lane 5: SW480; lane 6: RCA; lane 7: GEO; lane 8 FET; lane 9: xenograft Cx3; lane 10: normal colonic mucosa; lane 11: yeast tRNA; lane 12: probe alone (not RNase A digested); lane 13: SW1417 (long exposure). The fragments marked with arrowheads in lanes 5,6, and 13 were not present in the other samples.
Figure 7:
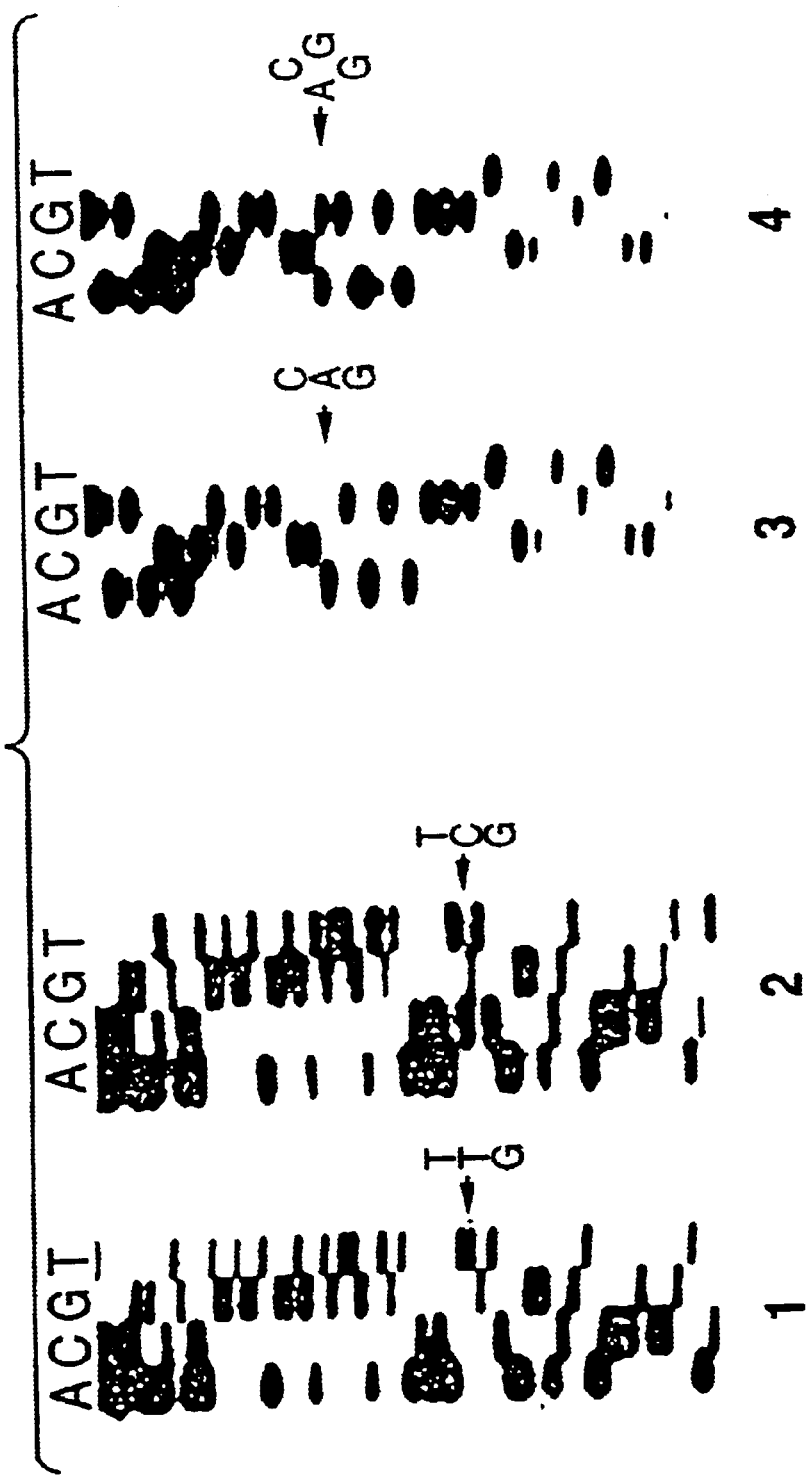
FIG. 7 diagrams the strategies used for amplification of p53 gene sequences. mRNA was used to generate a cDNA template for a polymerase chain reaction (PCR) employing primers P1 and P2 (top). The PCR product was 1.3 kb and included the entire coding region. Alternatively, total genomic DNA was used in a PCR reaction employing primers P3 and P4. The PCR product was 2.9 kb and included exons 4–9 (bottom). The numbered boxes indicate exons and the vertical dotted lines indicate the start (ATG) and stop (TGA) codons respectively.

The protected fragments were separated by electrophoresis through denaturing polyacrylamide gels; autoradiographs of the gels are presented in FIG. 6. The RNA was derived from: lane 1: S115, carcinoma biopsy; lane 2: SW1417; lane 3: SW948; lane 4: RKO; lane 5: SW480; lane 6: RCA; lane 7: GEO; lane 8: FET, lane 9: xenograft Cx3; lane 10: normal colonic mucosa; lane 11: yeast tRNA; lane 12: probe alone (not digested with RNase A); lane 13: SW1417 (long exposure). The fragments marked with arrowheads in lanes 5, 6 and 13 were not present in the other samples. The autoradiographic exposure time for lane 13 was 72 hours to allow adequate visualization of the new fragments; for all other lanes the exposure time was 10 hours.

The RNA from S carcinomas protected fragments of a different size than those seen with RNA from normal cells. In two cases, the new fragments were the major fragments detected (FIG. 6, lanes 6 and 13, arrowheads). In other cases, the new fragments were of minor intensity compared to the fully protected fragment (for example, SW480 in lane 5).

Such partial cleavages are not unexpected; the mutations in Cx3 and Cx1 were not detected by the RNase protection method (data not shown) and it is known that the majority of RNA sequence mismatches are partially or totally resistant to RNaseA.

Using similar techniques, five additional colorectal cancers, two breast tumors and one lung tumor have been examined for p53 gene mutations. In all cases, point mutations of the p53 gene were observed.

Example 7

This example demonstrates that a variety of types of tumors exhibit mutations in the p53 gene; that most tumors with allelic deletions of p53 have a mutation in the retained allele; that even some tumors with no p53 deletion have mutations in the p53 gene; and that the p53 mutations are clustered in four hot-spots on the gene.

A Variety of Tumors Carry p53 Mutations

We analyzed p53 sequences of tumors derived from the breast, lung, brain, colon, or mesenchyme. Tumors of these types have been previously shown to exhibit frequent deletions of chromosome 17p when studied by restriction fragment length polymorphism (RFLP) methods. To test for allelic deletions, tumor DNA samples were digested with HinfI and, following Southern transfer, hybridized sequentially to two probes (p144D6 (Kondoleon, et al., Nucleic Acids Res., vol. 15, p. 10605, 1987) and pYNZ22.1 (Nakamura, et al., Nucleic Acids Res., vol. 16, p. 5707, 1988)) detecting variable number of tandem repeat ("VNTR" or "mini-satellite") sequences. DNA samples from normal tissues exhibited two alleles with at least one of these probes in 29 of 31 different individuals tested. Because of this high degree of polymorphism, allelic loss could be assessed with greater than 95% certainty in cell lines and xenografts even when corresponding normal tissue was not available for comparison.

Nineteen tumors with allelic deletions of chromosome 17p were selected for sequence analysis. For tumor cell lines and for xenografts passaged in athymic nude mice, cDNA was generated from mRNA using oligo dT as a primer. A 1300 bp fragment including the entire p53 coding region was generated from the cDNA using PCR, and this fragment was cloned and sequenced in its entirety. For primary tumors, sufficient RNA was often not available for the first approach, and PCR was used to generate a 2.9 kb fragment from tumor DNA. This was the longest fragment that we could reproducibly amplify from the p53 locus, and included all of the exons found to contain mutations through the first approach.

RNA was purified using guanidinium isothiocyanate (Chomczynski, et al., Analytical Biochem., vol. 162, p. 156, 1987) and mRNA selected by binding to Messenger Affinity Paper (Amersham). cDNA was synthesized from 500–750 ng of mRNA using oligo dT as a primer. The oligo dT primer was removed by isopropanol precipitation; 10 μg of tRNA and sodium perchlorate (to a final aqueous concentration of 0.5M) were added to the reaction, and this was followed by addition of ½ volume of isopropanol (Kinzler, et al, Nucleic Acids Res., vol. 17, p. 3645, 1989; Haymerle, et al., Nucleic Acids Res., vol. 14, p. 8615, 1986). The cDNA was pelleted by centrifugation for 15 min. at room temperature and used in a 50 μl PCR reaction consisting of 35 cycles of 93° (1 minute), W 580 (1 minute), and 70° (2 minutes). Two μg of genomic DNA was used in a 200 μl PCR reaction consisting of 30 cycles at 95°. (1 minute), 58° (1 minute), and 70° (4 minutes). PCR reactions contained magnesium chloride at a final concentration of 2 mM. The primers used were P1: 5'-GGAATTCCACGACGGTGACACG-3' (SEQ ID NO:1); P2: 5'-GGAATTCAAAATGGCAGGGGAGGG-3' (SEQ ID NO:10); P3: 5'-GTAGGAATTCGTCCCAAGCAATGGATGAT-3' (SEQ ID NO:14); P4: 5'-CATCGAATTCTGGAAACTTTCCACTTGAT-3' (SEQ ID NO: 15). All primers had extraneous nucleotides comprising EcoRI sites at their 5' ends to facilitate cloning. The PCR products were digest with EcoRI, fractionated by electrophoresis, and following purification from agarose, ligated to EcoRI digested Bluescript vectors (Stratagene). Individual clones were sequenced with primers derived from the p53 coding and intron sequences (Buchman, et al., Gene, vol. 70, p. 245, 1988) using T7 polymerase and the TDMN sequencing method described in Del Sal, et al., Biotech., vol. 7, p. 514, 1989.

Thirteen of the tumors were found to contain a single missense mutation; two tumors each contained two mutations; one tumor contained a frame-shift mutation at codon 293; and no mutation was detected in four tumors (Table 1). The PCR reaction is known to be associated with a relatively high rate of base misincorporation (Saiki, et al. Science, vol. 239, p. 487, 1988), and we confirmed this observation by noting several sequence variants (13 out of 34,000 bp sequenced) in individual clones that were not reproducibly present in other PCR reactions from the same tumor sample. All of the mutations listed in Table 1 were confirmed by performing a second PCR reaction and re-sequencing the products en masse as described below.

TABLE 1

P53 GENE MUTATIONS IN HUMAN TUMORS

| Tumor # | Tumor Name | Tumor Type[a] | Tumor Cells Tested[b] | # of 17p Alleles[c] | Codon (Nucleotide) | Mutation (Nucleo-Amino Acid) |
|---|---|---|---|---|---|---|
| 1 | D263 | BRAIN | B,X | 1 | 175 GCG—CAC | Arg—His |
| 2 | D274 | BRAIN | X | 1 | 273 GCT—TGT | Arg—Cys |
| 3 | D303 | BRAIN | B,X | 1 | 216 GTG—ATG | Val—Met |
| 4 | D317 | BRAIN | B,X | 1 | 272 GTG—ATG | Val—Met |
| 5 | D247 | BRAIN | C | 1 | NONE DETECTED | |
| 6 | MDA 468 | BREAST | C | 1 | 273 CGT—CAT | Arg—His |
| 7 | T470 | BREAST | C | 1 | 194 CTT—TTT | Leu—Phe |
| 8 | BT123 | BREAST | B | 1 | NONE DETECTED | |
| 9 | 1012 | LUNG | B | 1 | 293 DELETED a G Frameshift | |
| 10 | 5855 | LUNG | B | 1 | NONE DETECTED | |
| 11 | H231 | LUNG | C | 2 | 134 TTT—TTA | Phe—Leu |
| 12 | 88-3/14 | NFS | B,C | 1 | 179 CAT—TAT | His—Tyr |
| 13 | Cx4A | COLON | B,X | 1 | 239 AAC—AGC | Asn—Ser |
| 14 | Cx5A | COLON | X | 1 | 248 CGG—TGG | Arg—Trp |
| 15 | Cx6A | COLON | X | 1 | 132 AAG—AAC | Lys—Asn |
|  |  |  |  |  | 133 ATG—TTG | Met—Leu |
| 16 | Cx7A | COLON | B,X | 2 | 281 GAC—GGC | Asp—Gly |
| 17 | CX19A | COLON | X | 2 | NONE DETECTED | |
| 18 | Cx20A | COLON | B,X | 1 | 175 CGC—CAC | Arg—His |
| 19 | Cx22A | COLON | X | 1 | 175 CGC—CAC | Arg—His |
| 20 | Cx26A | COLON | X | 1 | 141 TGC—TAC | Cys—Tyr |
| 21 | SW480 | COLON | C | 1 | 273 CGT—CAT | Arg—His |
|  |  |  |  |  | 309 CCC—TCC | Pro—Ser |
| 22 | SW837 | COLON | C | 1 | 248 CGG—TGG | Arg—Trp |

[a]The brain tumors were glioblastoma multiforme; the colon and breast tumors were adenocarcinomas, the NFS tumor was a neurofibrosarcoma developing in a patient with type I neurofibromatosis; H231 was a small cell carcinoma of the lung, and the other two lung tumors were non-small cell carcinomas.
[b]B = tumor biopsy; C = cell line passage in vitro; X = xenograft derived from biopsy, passaged in athymic nude mice. Whenever two sources of tumor cells are listed, both contained the indicated mutation.
[c]The number of alleles was determined by RFLP analysis as described in the text.

Six p53 Mutations are Somatic Mutations

Two observations indicated that the nucleotide substitutions described in Table I represented somatic mutations. First, none of these presumptive mutations have been observed in the sequences of human p53 genes derived from normal cells, SV40 transformed fibroblasts, or lymphoblastoid cell lines (Zakut-Houri, et al., EMBO, vol. 4, p. 1251, 1985; Lamb, et al., Mol. Cell. Biol., vol. 6, p. 1379, 1986; Matlashewski, Mol. Cell Biol., vol. 7, p. 961, 1987; Harris, et al., Mol. Cell. Biol., vol. 6, p. 4650, 1986; Matlashewski, et al., EMBO J., vol. 3, p. 3257, 1984 and our unpublished data). Second, in 6 cases (tumors #2, 3, 9, 12, 13, 16), normal tissue from the patients whose tumors are described in Table I were available for study. To test for the presence of the presumptive mutations (in the heterozygous state) in the germline of these patients, a strategy was devised which employed both PCR and cloning. Although direct sequencing of PCR products has been shown to be possible by several methods, we found that none of the published methods could be reproducibly applied to all parts of the p53 coding region. To circumvent this difficulty, we cloned the PCR products into a phagemid vector and used the DNA pooled from 103 to 104 independent phage clones as a template for DNA sequencing.

PCR reactions were carried out as described above and the reaction products digested with EcoRI. The entire reaction was ligated to 0.25 µl of lambda ZAP phage vector arms (Stratagene) and packaged using ¼ of a GIGA-PACK extract (Stratagene). E. coli BB4 cells were then infected, and $10^3$–$10^4$ phage clones plated on a 7 cm petri dish. The lambda ZAP vector contains the sequences for a phagemid into which the PCR inserts were cloned, and single stranded DNA phage can be rescued from the lambda phage clones using a helper phage (Short, et al., Nucleic Acids Res., vol. 16, p. 7583, 1988). An overnight culture of XL-I Blue cells (Stratagene) was grown in 0.4% maltose and resuspended in 1.5 volumes of 10 mM magnesium sulfate. Phages were eluted from the 7 cm dish in 5 ml phage dilution buffer (100 mM sodium chloride, 10 mM magnesium sulfate, 20 mM Tris, ph 7.5, 0.02% gelatin) for 2 hours at room temperature with gentle agitation. Fifty µl of eluate was used to infect 200 µl of XL-I Blue cells (Stratagene) in the presence of 1 µl helper phage R408 ($10^{11}$ PFU/ml). After 15 min. at 37°, 5 ml of 2×YT broth was added and the culture shaken for 3 hours at 37°, then heated to 70° for 20 min. Cell debris was pelleted at 3000 g for 5 min., and 10 µl of the supernatant, containing single-stranded DNA phage, was used to infect 200 µl of XL-1 Blue cells prepared as described above. After 15 min. at 37°, 100 µl of the mixture (containing over $10^4$ clones determined by titration on XL-1 Blue cells) was inoculated into 50 ml L-Broth and shaken overnight at 37°. Double-stranded DNA was isolated by a rapid alkaline lysis technique (Birnboim, et al., Nucleic Acids Res., vol. 7, p. 1513, 1979) and sequenced as described above. The primer used for sequencing in panels 1 and 2 was 5'-GAGGCAAGCAGAGGTGG-3' (SEQ ID NO: 16). The primer used for sequencing in panels 3 and 4 was 5'-TGGTAATCTACTGGGACG-3' (SEQ ID NO: 17).

Figure 8:
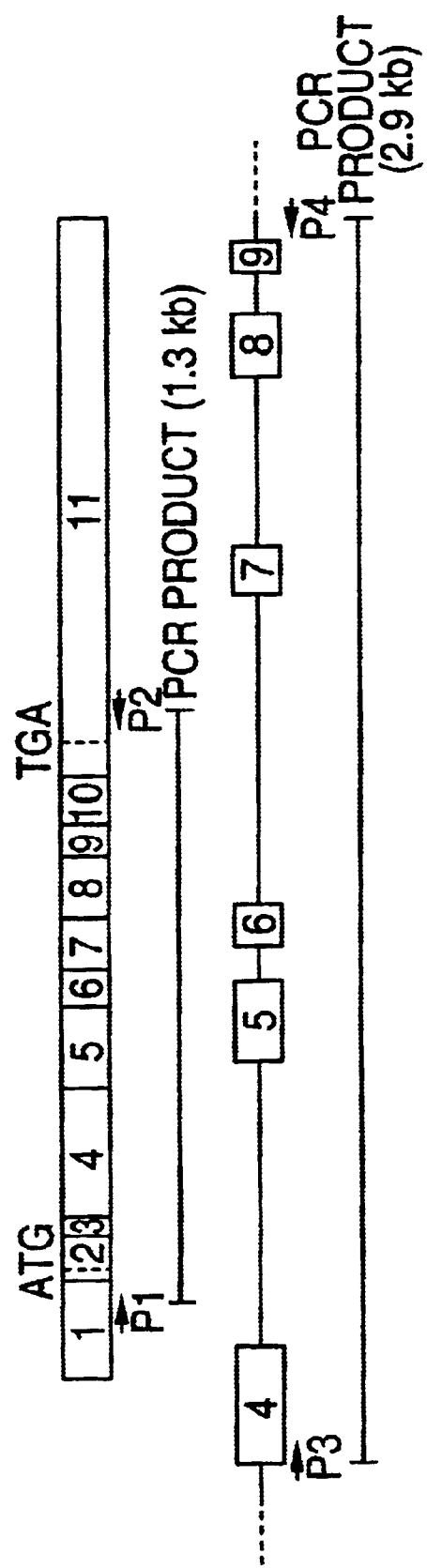
FIG. 8 shows examples of sequencing reactions demonstrating p53 gene mutations. The templates used for the sequencing reactions shown in panels 1–4 consisted of pools of greater than 103 clones generated from PCR products. Tumor #13 genomic DNA contained a mutation at codon 239 (antisense GCT, Panel 2), instead of the wild type sequence (GTT) found in the genomic DNA from normal lymphocytes from the same patient (Panel 1). Panel 4 shows a sequencing reaction of pooled cDNA clones from tumor #16 showing that both wild-type codon 281 (GAC) and mutant codon 281 (GGC) were both expressed. Only the wild type sequence (GAC) was found in pooled genomic DNA clones from normal lymphocytes of this patient (Panel 3).

This procedure resulted in sequence data quality as high as that produced using individual plasmid DNA clones as templates, and was used to demonstrate that in each of the six cases noted above, the mutations in the tumor DNA were not present in the germline of the patient (examples in FIG. 8).

Two Tumors With No Allelic Loss of p53 Carried p53 Mutations

The data described above indicated that most tumors with one 17p allele contained a mutation of the p53 gene in the remaining allele. To begin to assess the status of tumors which had not lost a 17p allele, we examined cDNA clones from three such tumors. In each case, two cDNA clones derived from PCR products, generated as described above were sequenced. In one case (tumor #11), both clones contained a single point mutation at codon 134 (Table I). In the second case (tumor #16), one clone contained a point mutation at codon 281 and one clone was wild type. In the third case (tumor #17), both clones were wild type. To assess the relative expression levels of the mutant alleles, the sequencing strategy employing pooled phage clones was utilized with cDNA from tumor mRNA as a template. In tumor number #11, only the mutant allele was expressed (data not shown); in tumor #16, the mutant and wild type alleles were expressed at approximately equal levels (FIG. 8, Panel 4).

The p53 Mutations are Clustered Along the Gene

Figure 9:
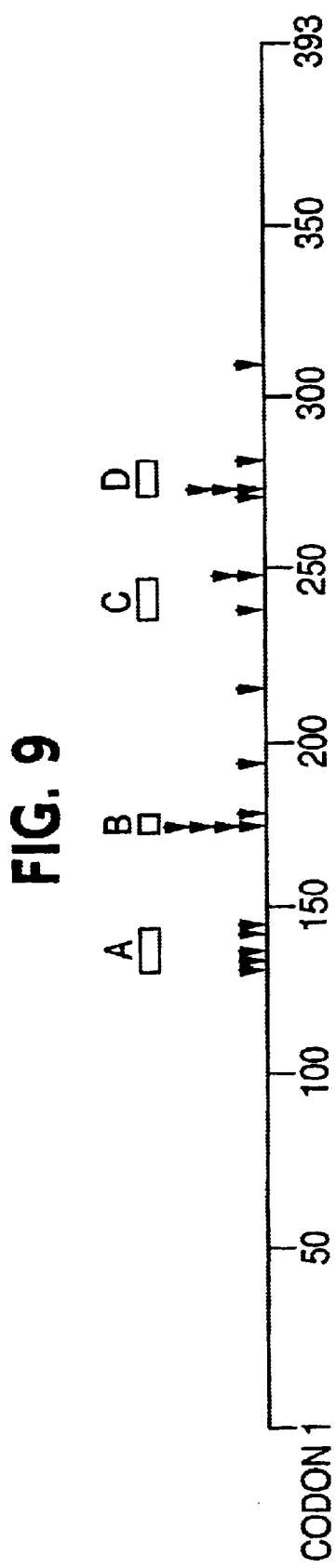
FIG. 9 maps the p53 point mutations involved in human cancer. Each of the missense mutations listed in Table 1 is indicated with an arrow. In addition, the two point mutations described previously (Baker, et al., Science, vol. 244, p. 217, 1989) in human cancers (at codons 143 and 175) are also included. The four regions containing most (86%) of the mutations are indicated by the black bars marked A–D.

Altogether, 20 point mutations (19 missense, 1 frameshift) were identified in the present example. These are mapped in FIG. 9, together with the two human p53 gene missense mutations previously described (Baker, et al., Science, vol. 244, p. 217, 1989). Several features are notable. Although the sample size is limited, the mutations tended to be clustered in four hotspots which accounted for 86% of the 21 missense mutations (5 mutations in region A, codons 132–143; five mutations in region B, codons 174–179; 3 mutations in region C, codons 236–248; 5 mutations in region D, codons 272–281). There have been two missense mutations identified in murine tumor cells, both in the carcinogen-induced fibrosarcoma cell line Meth A: one allele contained a mutation in region A, and the other contained one mutation in region C and one mutation in region D (Finlay, et al., Mol. Cell. Biol., vol. 8, p. 531, 1988; Eliyahu, et al., Oncogene, vol. 3, p. 313, 1988). Interestingly, the four hotspots for in vivo mutation coincided exactly with the four most highly conserved regions of the p53 gene, previously identified (Soussi, et al., Oncogene, vol. 1, p. 71, 1987). Of the 41 amino acids contained within regions A–D, 93% are identical in the wild-type p53 genes of amphibian, avian, and mammalian species, compared to a conservation of only 51–57% over the entire p53 coding sequence. The clustering of mutations and evolutionary conservation of regions A–D suggest that they play a particularly important role in mediating the normal function of the p53 gene product.

Example 8

This example shows that expression of the wild-type p53 gene in human colorectal carcinoma cells dramatically inhibits their growth and that a mutant p53 gene cloned from a human colorectal carcinoma was incapable of exerting such inhibition.

The colorectal carcinoma lines SW480 and SW837, which are representative of 75% of colon carcinomas, have each lost one copy of chromosome 17p (including the p53 gene) and the remaining p53 allele is mutated (Baker, et al., Science 244, 217 (1989); Nigro et al, Nature 342, 705 (1989)). The SW837 line contains an arginine to tryptophan mutation at codon 248 (Nigro, supra). The SW480 line contains two point mutations, arginine to histidine at codon 273 and proline to serine at codon 309 (Nigro, supra.). The substitutions at codon 248 and 273 are typical of those observed in human tumors, occurring within two of the four mutation "hot spots" (Nigro, supra).

For the transfection studies, we constructed a vector, pCMV-Neo-Bam, engineered to contain two independent transcription units. The expression vector pCMV-Neo-Bam was derived from plasmid BCMGNeo-mIL2 (Karasuyama, et al., J. Exp. Med. 169, 13 (1989) by excision of the human beta globin sequences and bovine papilloma virus sequences with BamHI and NotI. Next, the interleukin 2 (IL-2) sequences present at the unique XhoI site were removed, and the XhoI site was changed to a BamHI site by linker addition. The vector included CMV promoter/enhancer sequences, which could drive expression of the insert at the BamHI site, and splicing and polyadenylation sites derived from the rabbit beta globin gene, which ensured proper processing of the transcribed insert in the cells. A pBR322 origin of replication and b-lactamase gene facilitated growth of the plasmid in E. coli. The plasmid conferred geneticin resistance through expression of the neomycin resistance gene under separate control of an HSV thymidine kinase promoter. The first transcription unit comprised a cytomegalovirus (CMV) promoter/enhancer upstream of a site for insertion of the cDNA sequences to be expressed, and splice and polyadenylation sites to ensure appropriate processing. The second transcription unit included a herpes simplex virus (HSV) thymidine kinase promoter/enhancer upstream of the neomycin resistance gene, allowing for selection of transfected cells in geneticin.

A wild-type p53 cDNA was inserted into pCMV-Neo-Bam to produce pC53-SN3. Similarly, a vector, pC53-SCX3, expressing a mutant cDNA from human colorectal tumor CX3, was also constructed. The only difference between pC53-SN3 and pC53-SCX3 was a single nucleotide (C to T) resulting in a substitution of alanine for valine at p53 codon 143 in pC53-SCX3. The two constructs were made as follows: a 1.8-kb XbaI fragment, extending from nucleotide −130 to 1671 relative to the translation initiation site, was isolated from wild-type or CX3 cDNA clones. The fragment was blunt-ended with the Klenow fragment of DNA polymerase, ligated to BamHI linkers, and cloned into the unique BamHI site in the expression vector pCMV-Neo-Bam.

The constructs were transfected into SW837 and SW480 cells (obtained from the American Type Culture Collection, Rockville, Maryland), and geneticin-resistant colonies were counted 3 weeks later. Cells transfected with pC53-SN3 formed five-to tenfold fewer colonies than those transfected with pC53-SCX3 in both recipient cell types (Table 2).

TABLE 2

Colony formation after transfection with wild-type and mutant p53 expression vectors. For each experiment, one or two 75-cm$^2$ flasks were transfected, and the total colonies counted after 3 to 4 weeks of selection in geneticin (0.8 mg/ml). Exp. experiment.

| Cell line | Exp. | No. of geneticin-resistant colonies formed | |
|---|---|---|---|
| | | pC53-SCX3 (mutant) | pC53-SN3 (wild-type) |
| SW837 | 1 | 754 | 66 |
| | 2 | 817 | 62 |
| SW480 | 1 | 449 | 79 |
| | 2 | 364 | 26 |

TABLE 2-continued

Colony formation after transfection with wild-type and mutant p53 expression vectors. For each experiment, one or two 75-cm² flasks were transfected, and the total colonies counted after 3 to 4 weeks of selection in geneticin (0.8 mg/ml). Exp. experiment.

| Cell line | Exp. | No. of geneticin-resistant colonies formed | |
|---|---|---|---|
| | | pC53-SCX3 (mutant) | pC53-SN3 (wild-type) |
| RKO | 1 | 1858 | 190 |
| | 2 | 1825 | 166 |
| VACO 235 | 1 | 18 | 16 |
| | 2 | 26 | 28 |

In both SW837 and SW480 cells, the number of colonies produced by the expression vector pCMV-Neo-Bam (without a p53 cDNA insert) was similar to that induced by the pC53-SCX3 construct.

Figure 10:
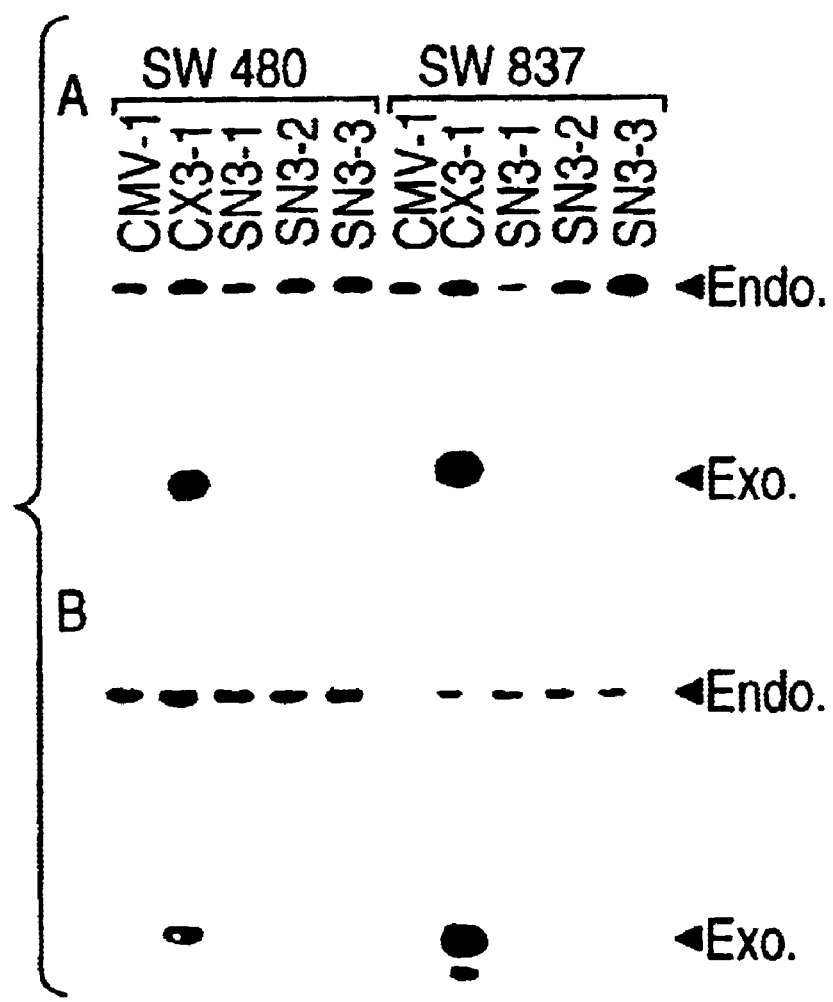
FIG. 10A shows RNase protection analysis of transfected clonal lines. A labeled antisense p53 probe was hybridized with total cellular RNA, and digested with RNase A. Endogenous RNA included all sequences represented in the labeled probe. Exogenous p53 RNA produced from the expression vectors extended only about ⅔ of the length of the probe.
FIG. 10B shows Southern blot analysis of transfected clonal lines. The exogenous p53 gene was present on a 1.8 kb BamHI fragment. The endogenous p53 gene gave rise to a 7.8 kb BamHI fragment. Other sized fragments presumably arose by rearrangements.

These results suggest that the wild-type p53 gene inhibits the clonal growth of both the SW837 and SW480 cell lines; however, a significant number of colonies formed after transfection of the wild-type construct. If wild-type p53 expression were truly inhibitory to cell growth, one would expect that no colonies would form or that p53 expression in the colonies that did form would be reduced compared to that produced with the mutant p53 cDNA construct. To evaluate this issue, we expanded independent SW480 and SW837 colonies into lines, and ribonuclease (RNase) protection analysis was performed to determine the amount of p53 mRNA expressed from the exogenously introduced sequences. Twelve of 31 lines (38%) derived from transfection with the pC53-SCX3 construct were found to express the exogenous mutant p53 mRNA. This percentage was consistent with results expected in human cells transfected with a vector containing two independent transcription units. Previous studies have shown that, in contrast to rodent cells, primate cells are able to integrate only a small amount of foreign DNA (approximately 6 kb), so that only 10 to 30% of clones selected for the expression of one transcription unit also contain the second unit in an intact form (F. Collabere-Garapin, et al., Gene 50, 279 (1986); Hoeijmakers, et al., Exp. Cell Res., 169, 111 (1987); Mayne et al., Gene 66, 65 (1988), Dean, et al., Exp. Cell Res., 183, 473 (1989). In contrast, no expression of exogenous p53 wild-type mRNA was seen in any of 21 clonal lines established from either SW480 or SW837 cells transfected with the pC53-SN3 vector (FIG. 10A). These RNase protection results were supported by analysis of the exogenous p53 DNA sequences within the clones. All of the p53-expressing clones derived from the pC53-SCX3 transfection contained an intact copy of the exogenous p53 gene (FIG. 10B). In contrast, in all the clones derived from the pC53-SN3 transfection, the exogenous p53 sequences were deleted or rearranged (FIG. 10B).

The results from individual clones were further supported by the analysis of pooled clones, in which numerous colonies could be simultaneously assessed. Forty or more clones from two to three separate transfection experiments were pooled and analyzed approximately 3 weeks after transfection. RNase protection studies showed substantial expression of wild-type sequences was not detectable (FIG. 11A). Results from Southern (DNA) blotting were consistent with the RNase protection studies, in that pooled colonies from the wild-type transfectants had no detectable unrearranged exogenous p53 sequences, in contrast to the intact p53 sequences in colonies derived from the mutant p53 cDNA expression vector (FIG. 11B).

The conclusions made from the above experiments are dependent on the assumption that p53 protein was produced in the transfected cell lines. Clones containing exogenous mutant p53 sequences produced p53 mRNA at a concentration 1.5 to 3.5 time higher than that produced by the endogenous p53 gene (FIGS. 10A and 11A). Immunoblot analysis showed that there was a concomitant small increase in p53 protein expression in the transfectants (1.5- to 3-fold) compared to the untransfected cells. However, this increase was difficult to measure quantitatively, since these cells produced significant amounts of endogenous p53 protein that (unlike endogenous p53 mRNA) could not be distinguished from that produced by the vectors. To confirm that transfected human cells expressed p53 protein from our constructs, we studied an additional colorectal carcinoma cell line (RKO). RKO cells were obtained through the generosity of M. Brattain. Although RKO cells did not contain a mutation within the susceptible p53 coding sequences, i.e., exons 5–9, they expressed low concentrations of p53 mRNA compared to normal colorectal mucosa or the other lines studied and did not produce detectable amounts of protein.

Results of colony formation assays in transfected RKO cells were similar to those in SW480 and SW837 cells. Colony formation by wild-type p53 gene transfectants occurred with a tenfold decrease in efficiency compared to the mutant p53 construct (Table 2). Immunocytochemical detection of p53 protein in transfected RKO cells was done as follows: approximately $5 \times 10^4$ cells were cytocentrifuged onto polylysine-coated slides, fixed for 10 min in formalin, and permeabilized for 5 min in 0.5% Triton X-100. A mouse monoclonal antibody against human p53 protein (Ab1801) in combination with the ABC immunoperoxidase system (Vector Laboratories), was used for immunocytochemical detection of p53 protein (Banks, et al., Eur. J. Biochem. 159, 529 (1986)). Ten to 20 randomly selected microscopic fields were analyzed per slide. These observations are consistent with the greater stability of mutant compared to wild-type p53 protein noted previously (C. A. Finlay et al., Mol. Cell Biol. 8, 531 (1988)). However, transient mRNA expression was also significantly lower in the SN3 transfectants compared to the SCX3 transfectants at 48 and 96 hours, supporting the idea that RKO cells expressing wild-type p53 were at a selective disadvantage compared to those producing mutant p53 products.

To obtain additional evidence that cells expressing p53 were inhibited in their growth potential, we examined the effect of p53 gene expression on DNA synthesis in transfected RKO cells were labeled with [³H]thymidine for 2 hours. The cells were subsequently fixed, immunocytochemically stained for the presence of p53 protein, and autoradiographed. The number of cells undergoing DNA replication was only slightly lower in cells producing exogenous mutant p53 protein than in cells that did not express any detectable p53 protein. Expression of the wild-type protein, however, dramatically inhibited the incorporation of thymidine (Table 3).

TABLE 3

Immunocytochemistry and [³H]thymidine incorporation of transfected RKO cells.

| Plasmid | Percent of cells expressing p53 protein at | | | | Percent of cells incorporating [³H]thymidine in | |
|---|---|---|---|---|---|---|
| | 6 hrs | 24 hrs | 48 hrs | 96 hrs | p53 expressors | p53 non-expressors |
| pC53-SCX3 | 1.0 | 11 | 4.3 | 2.0 | 24 | 31 |
| pC53-SN3 | 1.9 | 5.2 | 0.3 | 0.2 | 1.7 | 33 |

These results all suggested that wild-type p53 exerted an inhibitory effect on the growth of carcinoma cells in vitro. To evaluate whether this inhibitory effect was cell type-specific, we transfected colorectal epithelial cells derived from a benign tumor of the colon (the VACO 235 adenoma cell line). VACO 235 cells are described by J. K. V. Willson et al., Cancer Res., 47, 2704 (1987). Previous studies have shown that most adenomas contain two copies of chromosome 17p and express wild-type p53 mRNA at concentrations similar to that of normal colonic mucosa. Analogously, the p53 alleles of the VACO 235 cell line were sequenced (exons 5–9) and found to be wild-type and the expression of p53 mRNA was found to be similar to that of normal colorectal mucosa. In contrast to the results seen with SW480, SW837, and RKO cells, the pC53-SN3 and pC53-SCX3 constructs produced similar numbers of geneticin-resistant colonies after transfection of the VACO 235 line (Table 2). We considered, however, that the most definitive test for differential growth inhibition by wild-type versus mutant p53 genes involved analysis of exogenous p53 expression in pooled transfectants. Through such analysis, a large number of colonies could be examined simultaneously and the expression of exogenous mutant and wild-type p53 genes directly compared. Striking differences in the relative expression from the transfected genes were seen in all three carcinoma cell lines tested. VACO 235 transfectants, however, expressed similar amounts of exogenous p53 mRNA from either pC53-SN3 (wild-type) or pC53-SCX3 (mutant) p53 constructs (FIG. 11A).

In summary, our results suggest that expression of the wild-type p53 gene in colorectal carcinoma cell lines was incompatible with proliferation. The inhibitory effects of wild-type p53 were specific in two ways. First, a single point mutation in a p53 gene construct abrogated its suppressive properties as measured by three separate assays (colony formation, exogenous p53 expression in transfected clones, and thymidine incorporation). The CX3 mutant provided a control for gene specificity as it contained only one conservative mutation, resulting in a substitution of one hydrophobic amino acid (alanine) for another (valine) at a single codon. Second, the growth-suppressive effect of the wild-type p53 construct was cell type-specific. Introduction of the wild-type vector into the VACO 235 adenoma cell line had no measurable inhibitory effect compared to the mutant p53 vector. There are several differences between the cell lines that could account for the differential effect of the introduced vectors. Regardless of the basis for the difference, the results with the VACO 235 cell line minimize the possibility that the wild-type p53 construct had some nonspecific, toxic effect on recipient cells; the effect was cell type-dependent.

The transfection and expression results of Table 2 and FIG. 11A suggest that cells at the premalignant stages of tumor progression (VACO 235) may be less sensitive to the inhibitory effects of wild-type p53 than malignant cells (SW480, SW837, and RKO). This hypothesis is consistent with previous results that suggest the wild-type p53 is less inhibitory to the growth of normal rat embryo fibroblasts than to their oncogene-transfected derivatives. Finlay et al., Cell 57, 1083 (1989); Eliyahu et al., Proc. Natl. Acad. Sci. USA, 86, 8763 (1989). This sensitivity may only be relative: expression of the wild-type gene at high concentrations might inhibit the growth of any cell type, including non-neoplastic cells, by overwhelming normal regulatory processes such as phosphorylation. Samad et al., Proc. Natl. Acad. Sci. USA, 83, 897 (1986); Meek et al., Mol. Cell Biol. 8, 461 (1988). Genetic alterations that occur during the progression of colorectal tumors may increase the sensitivity of cells to p53 inhibition, making wild-type p53 expression a key, rate-limiting factor for further tumor growth and expansion. At this point, and not before, mutations in the p53 gene would confer a selective growth advantage to cells in vivo, which would explain the frequent occurrence of p53 gene mutations and allelic loss only in the more advanced stages of colorectal tumorigenesis.

What is claimed is:

1. A method of supplying wild-type p53 gene function to a cell which has lost said gene function by virtue of a mutation in a p53 gene, comprising:

introducing a portion of a human wild-type p53 gene into a human cell which has lost said gene function such that said portion is expressed in the cell, said portion encoding a part of human wild-type p53 protein which is required for non-neoplastic growth of said cell, whereby wild-type p53 gene function is supplied to the cell.

2. The method of claim 1 wherein said portion corresponds to a region of the p53 gene in the cell which contains the mutation.

* * * * *

SEQUENCE LISTING

<160> NUMBER OF SEQ ID NOS: 17

<210> SEQ ID NO 1
<211> LENGTH: 22
<212> TYPE: DNA
<213> ORGANISM: Homo sapiens

<400> SEQUENCE: 1
ggaattccac gacggtgaca cg                                    22

<210> SEQ ID NO 2
<211> LENGTH: 24
<212> TYPE: DNA
<213> ORGANISM: Homo sapiens

<400> SEQUENCE: 2
ggaattcggt gtaggagctg ctgg                                                      24

<210> SEQ ID NO 3
<211> LENGTH: 23
<212> TYPE: DNA
<213> ORGANISM: Homo sapiens

<400> SEQUENCE: 3
ggaattccca gaatgccaga ggc                                                       23

<210> SEQ ID NO 4
<211> LENGTH: 25
<212> TYPE: DNA
<213> ORGANISM: Homo sapiens

<400> SEQUENCE: 4
ggaattcatg tgctgtgact gcttg                                                     25

<210> SEQ ID NO 5
<211> LENGTH: 21
<212> TYPE: DNA
<213> ORGANISM: Homo sapiens

<400> SEQUENCE: 5
ggaattccac acccccgccc g                                                         21

<210> SEQ ID NO 6
<211> LENGTH: 22
<212> TYPE: DNA
<213> ORGANISM: Homo sapiens

<400> SEQUENCE: 6
ggaattcatg ccgcccatgc ag                                                        22

<210> SEQ ID NO 7
<211> LENGTH: 24
<212> TYPE: DNA
<213> ORGANISM: Homo sapiens

<400> SEQUENCE: 7
ggaattctga ctgtaccacc atcc                                                      24

<210> SEQ ID NO 8
<211> LENGTH: 23
<212> TYPE: DNA
<213> ORGANISM: Homo sapiens

<400> SEQUENCE: 8
ggaattctcc atccagtggt ttc                                                       23

<210> SEQ ID NO 9
<211> LENGTH: 24
<212> TYPE: DNA
<213> ORGANISM: Homo sapiens

<400> SEQUENCE: 9
ggaattccca acaacaccag ctcc                                                      24

<210> SEQ ID NO 10
<211> LENGTH: 23
<212> TYPE: DNA
<213> ORGANISM: Homo sapiens -continued

```
<400> SEQUENCE: 10
gaattcaaaa tggcagggga ggg                                        23

<210> SEQ ID NO 11
<211> LENGTH: 21
<212> TYPE: DNA
<213> ORGANISM: Homo sapiens

<400> SEQUENCE: 11
ttcctcttcc tgcagtactc c                                          21

<210> SEQ ID NO 12
<211> LENGTH: 18
<212> TYPE: DNA
<213> ORGANISM: Homo sapiens

<400> SEQUENCE: 12
gacgcgggtg ccgggcgg                                              18

<210> SEQ ID NO 13
<211> LENGTH: 24
<212> TYPE: DNA
<213> ORGANISM: Homo sapiens

<400> SEQUENCE: 13
cggaattcag gcggctcata gggc                                       24

<210> SEQ ID NO 14
<211> LENGTH: 29
<212> TYPE: DNA
<213> ORGANISM: Homo sapiens

<400> SEQUENCE: 14
gtaggaattc gtcccaagca atggatgat                                  29

<210> SEQ ID NO 15
<211> LENGTH: 29
<212> TYPE: DNA
<213> ORGANISM: Homo sapiens

<400> SEQUENCE: 15
catcgaattc tggaaacttt ccacttgat                                  29

<210> SEQ ID NO 16
<211> LENGTH: 17
<212> TYPE: DNA
<213> ORGANISM: Homo sapiens

<400> SEQUENCE: 16
gaggcaagca gaggtgg                                               17

<210> SEQ ID NO 17
<211> LENGTH: 18
<212> TYPE: DNA
<213> ORGANISM: Homo sapiens

<400> SEQUENCE: 17
tggtaatcta ctgggacg                                              18
```